(12) United States Patent
Weiner et al.

(10) Patent No.: US 7,738,942 B2
(45) Date of Patent: Jun. 15, 2010

(54) DEVICE AND METHOD FOR PREVENTING MAGNETIC-RESONANCE IMAGING INDUCED DAMAGE

(75) Inventors: Michael L. Weiner, Webster, NY (US); Victor R. Miller, Clarence, NY (US); Patrick R. Connelly, Rochester, NY (US); Jeffrey L. Helfer, Webster, NY (US)

(73) Assignee: Medtronic, Inc., Minneapolis, MN (US)

( * ) Notice: Subject to any disclaimer, the term of this patent is extended or adjusted under 35 U.S.C. 154(b) by 1863 days.

(21) Appl. No.: 10/795,746

(22) Filed: Mar. 8, 2004

(65) Prior Publication Data

US 2005/0113876 A1 May 26, 2005

Related U.S. Application Data

(62) Division of application No. 10/405,154, filed on Apr. 2, 2003, now abandoned.

(51) Int. Cl.
*A61B 5/05* (2006.01)
*H05K 9/00* (2006.01)
*A61N 1/00* (2006.01)

(52) U.S. Cl. .................. 600/411; 600/421; 361/816; 174/350; 607/2

(58) Field of Classification Search .......... 600/407, 600/410, 411, 412, 421; 427/216, 217; 174/350, 174/377; 324/309; 361/816, 818; 607/2, 607/9, 119
See application file for complete search history.

(56) References Cited

U.S. PATENT DOCUMENTS

| | | | |
|---|---|---|---|
| 4,004,257 A * | 1/1977 | Geissler | 333/207 |
| 4,760,336 A | 7/1988 | Conolly | |
| 5,217,010 A * | 6/1993 | Tsitlik et al. | 607/9 |
| 5,393,928 A | 2/1995 | Cribb et al. | |
| 5,426,399 A | 6/1995 | Matsubayashi et al. | |
| 5,492,122 A | 2/1996 | Button et al. | |
| 5,523,534 A * | 6/1996 | Meister et al. | 174/36 |
| 5,658,164 A | 8/1997 | Parker | |
| 5,699,801 A | 12/1997 | Atalar et al. | |
| 5,711,300 A | 1/1998 | Schneider et al. | |
| 5,730,134 A | 3/1998 | Dumoulin et al. | |
| 5,827,997 A * | 10/1998 | Chung et al. | 174/388 |
| 5,837,940 A | 11/1998 | Moncrieff | |
| 5,841,075 A | 11/1998 | Hanson | |
| 5,847,324 A | 12/1998 | Farquhar et al. | |
| 5,916,161 A | 6/1999 | Ishihara et al. | |

(Continued)

OTHER PUBLICATIONS

Supplementary European Search Report for 04749543.7-1269 mailed Aug. 4, 2009.

*Primary Examiner*—Eric F Winakur
*Assistant Examiner*—Katherine L Fernandez
(74) *Attorney, Agent, or Firm*—Stephen W. Bauer; Michael J. Ostrom

(57) ABSTRACT

An electromagnetic shield has a first patterned or apertured layer having non-conductive materials and conductive material and a second patterned or apertured layer having non-conductive materials and conductive material. The conductive material may be a metal, a carbon composite, or a polymer composite. The non-conductive materials in the first patterned or apertured layer may be randomly located or located in a predetermined segmented pattern such that the non-conductive materials in the first patterned or apertured layer are located in a predetermined segmented pattern with respect to locations of the non-conductive materials in the second patterned or apertured layer.

54 Claims, 32 Drawing Sheets

U.S. PATENT DOCUMENTS

| | | |
|---|---|---|
| 6,134,478 A | 10/2000 | Spehr |
| 6,225,565 B1 | 5/2001 | Prysner |
| 6,284,971 B1 * | 9/2001 | Atalar et al. .................. 174/36 |
| 6,396,266 B1 | 5/2002 | Debbins et al. |
| 6,433,286 B1 | 8/2002 | Doberenz |
| 6,486,394 B1 | 11/2002 | Schmidt et al. |
| 6,506,972 B1 | 1/2003 | Wang |
| 6,610,931 B2 | 8/2003 | Perelman et al. |
| 6,615,069 B1 | 9/2003 | Komura et al. |
| 6,673,999 B1 | 1/2004 | Wang et al. |
| 6,765,144 B1 | 7/2004 | Wang et al. |
| 6,777,622 B2 | 8/2004 | Ueno et al. |
| 6,801,037 B1 | 10/2004 | Zhang |
| 2002/0133086 A1 | 9/2002 | Connelly et al. |
| 2002/0183796 A1 * | 12/2002 | Connelly ....................... 607/9 |
| 2003/0083726 A1 | 5/2003 | Zeijlemaker et al. |
| 2004/0199069 A1 | 10/2004 | Connelly et al. |
| 2004/0201971 A1 | 10/2004 | Fessler et al. |
| 2004/0238798 A1 | 12/2004 | Aisenbrey |
| 2004/0251042 A1 | 12/2004 | Weiner et al. |

* cited by examiner

DEVICE AND METHOD FOR PREVENTING MAGNETIC-RESONANCE IMAGING INDUCED DAMAGE

CROSS-REFERENCE TO RELATED U.S. PATENT APPLICATIONS

This application is a divisional of co-pending U.S. patent application Ser. No. 10/405,154, filed on Apr. 2, 2003. The entire contents of U.S. patent application Ser. No. 10/405,154 are hereby incorporated by reference.

FIELD OF THE PRESENT INVENTION

The present invention relates generally to a device and method for preventing magnetic-resonance imaging induced damage. More particularly, the present invention is directed to medical assist systems, which may include leads and other implantable or non-implantable components, that are shielded by segmented shielding to hardened or immune the systems from electromagnetic interference or insult, namely electromagnetic interference or insult in a magnetic-resonance imaging environment and to a modifiable magnetic-resonance imaging, which is, automatically or manually, responsive to sensed tissue temperature changes or known localized specific energy absorption ratios.

CROSS REFERENCE TO RELATED PATENT APPLICATIONS

The subject matter of the present application is related to the subject matter of co-pending U.S. patent application Ser. No. 09/885,867, filed on Jun. 20, 2001, entitled "Controllable, Wearable magnetic-resonance imaging-Compatible Cardiac Pacemaker With Pulse Carrying Photonic Catheter And VOO Functionality"; co-pending U.S. patent application Ser. No. 09/885,868, filed on Jun. 20, 2001, entitled "Controllable, Wearable magnetic-resonance imaging-Compatible Cardiac Pacemaker With Power Carrying Photonic Catheter And VOO Functionality"; co-pending U.S. patent application Ser. No. 10/037,513, filed on Jan. 4, 2002, entitled "Optical Pulse Generator For Battery Powered Photonic Pacemakers And Other Light Driven Medical Stimulation Equipment"; co-pending U.S. patent application Ser. No. 10/037,720, filed on Jan. 4, 2002, entitled "Opto-Electric Coupling Device For Photonic Pacemakers And Other Opto-Electric Medical Stimulation Equipment"; co-pending U.S. patent application Ser. No. 09/943,216, filed on Aug. 30, 2001, entitled "Pulse Width Cardiac Pacing Apparatus"; co-pending U.S. patent application Ser. No. 09/964,095, filed on Sep. 26, 2001, entitled "Process for Converting Light"; co-pending U.S. patent application Ser. No. 09/921,066, filed on Aug. 2, 2001, entitled "magnetic-resonance imaging-Resistant Implantable Device"; co-pending U.S. patent application Ser. No. 10/077,842, filed on Feb. 19, 2002, entitled "An Electromagnetic Interference Immune Tissue Invasive System"; co-pending U.S. patent application Ser. No. 10/077,823, filed on Feb. 19, 2002, entitled "An Electromagnetic Interference Immune Tissue Invasive System"; co-pending U.S. patent application Ser. No. 10/077,887, filed on Feb. 19, 2002, entitled "An Electromagnetic Interference Immune Tissue Invasive System"; co-pending U.S. patent application Ser. No. 10/077,883, filed on Feb. 19, 2002, entitled "An Electromagnetic Interference Immune Tissue Invasive System"; and co-pending U.S. patent application Ser. No. 10/077,958, filed on Feb. 19, 2002, entitled "An Electromagnetic Interference Immune Tissue Invasive System".

The entire content of each of the above noted co-pending U.S. patent applications (Ser. Nos. 09/885,867; 09/885,868; 10/037,513; 10/037,720; 09/943,216; 09/964,095; 09/921,066; 10/077,842; 10/077,823; 10/077,887; 10/077,883; and 10/077,958) is hereby incorporated by reference.

BACKGROUND OF THE PRESENT INVENTION

Magnetic-resonance imaging ("magnetic-resonance imaging") has been developed as an imaging technique adapted to obtain both images of anatomical features of human patients as well as some aspects of the functional activities of biological tissue. These images have medical diagnostic value in determining the state of the health of the tissue examined.

In a magnetic-resonance imaging process, a patient is typically aligned to place the portion of the patient's anatomy to be examined in the imaging volume of the magnetic-resonance imaging apparatus. Such an magnetic-resonance imaging apparatus typically comprises a primary magnet for supplying a constant magnetic field ($B_0$) which, by convention, is along the z-axis and is substantially homogeneous over the imaging volume and secondary magnets that can provide linear magnetic field gradients along each of three principal Cartesian axes in space (generally x, y, and z, or $x_1$, $x_2$ and $X_3$, respectively). The apparatus also comprises one or more radio-frequency coils that provide excitation and detection of the magnetic-resonance imaging signal.

The use of the magnetic-resonance imaging process with patients who have implanted or non-implanted medical assist devices; such as, but not limited to, cardiac assist devices, implanted insulin pumps, catheter guide wires, leads for neurostimulation probes, intraluminal coils, guided catheters, temporary cardiac pacemakers, temporary esophageal pacemakers; often presents problems.

For a specific example, as is known to those skilled in the art, implantable devices (such as implantable pulse generators (IPGs) and cardioverter/defibrillator/pacemakers (CDPs)) are sensitive to a variety of forms of electromagnetic interference (EMI) because these enumerated devices include sensing and logic systems that respond to low-level electrical signals emanating from the monitored tissue region of the patient and that these devices may also have metal wire leads, which can act as antenna and provide a path for the induced energy to travel to and possibly damage power sensitive circuitry.

Since the sensing systems and conductive elements of these medical assist devices are responsive to changes in local electromagnetic fields, the medical assist devices are vulnerable to external sources of severe electromagnetic noise, and in particular, to electromagnetic fields emitted during the magnetic-resonance imaging (magnetic-resonance imaging) procedure. Thus, patients with medical assist devices are generally advised not to undergo magnetic-resonance imaging (magnetic-resonance imaging) procedures.

To more appreciate the problem using a specific illustration, namely the use of implantable cardiac assist devices during a magnetic-resonance imaging process, will be briefly discussed.

The human heart may suffer from two classes of rhythmic disorders or arrhythmias: bradycardia and tachyarrhythmia. Bradycardia occurs when the heart beats too slowly, and may be treated by a common implantable pacemaker delivering low voltage (about 3 V) pacing pulses.

The common implantable pacemaker is usually contained within a hermetically sealed enclosure, in order to protect the operational components of the device from the aqueous environment of the body, as well as to protect the body from the device.

The common implantable pacemaker operates in conjunction with one or more electrically conductive leads, adapted to conduct electrical stimulating pulses to sites within the patient's heart and to communicate sensed signals from those sites back to the implanted device.

Furthermore, the common implantable pacemaker typically has a metal case and a connector block mounted to the metal case that includes receptacles for leads which may be used for electrical stimulation or which may be used for sensing of physiological signals. The battery and the circuitry associated with the common implantable pacemaker are hermetically sealed within the case. Electrical interfaces are employed to connect the leads outside the metal case with the medical device circuitry and the battery inside the metal case.

Electrical interfaces serve the purpose of providing an electrical circuit path extending from the interior of a hermetically sealed metal case to an external point outside the case while maintaining the hermetic seal of the case. A conductive path is provided through the interface by a conductive pin that is electrically insulated from the case itself.

Such interfaces typically include a ferrule that permits attachment of the interface to the case, the conductive pin, and a hermetic glass or ceramic seal that supports the pin within the ferrule and isolates the pin from the metal case.

A common implantable pacemaker can, under some circumstances, be susceptible to electrical interference such that the desired functionality of the pacemaker is impaired. For example, common implantable pacemaker requires protection against electrical interference from electromagnetic interference (EMI), defibrillation pulses, electrostatic discharge, or other generally large voltages or currents generated by other devices external to the medical device. As noted above, more recently, it has become crucial that cardiac assist systems be protected from magnetic-resonance imaging sources.

Such electrical interference can damage the circuitry of the cardiac assist systems or cause interference in the proper operation or functionality of the cardiac assist systems. For example, damage may occur due to high voltages or excessive currents introduced into the cardiac assist system by voltages or currents induced in the cardiac assist system circuitry or on the wire leads leading to and from the cardiac assist system circuitry.

Therefore, it is required that such voltages and currents be limited at the input of such cardiac assist systems, e.g., at the interface, Protection from such voltages and currents has typically been provided at the input of a cardiac assist system by the use of one or more zener diodes and one or more filter capacitors.

For example, one or more zener diodes may be connected between the circuitry to be protected, e.g., pacemaker circuitry, and the metal case of the medical device in a manner which grounds voltage surges and current surges through the diode(s). Such zener diodes and capacitors used for such applications may be in the form of discrete components mounted relative to circuitry at the input of a connector block where various leads are connected to the implantable medical device, e.g., at the interfaces for such leads.

However, such protection, provided by zener diodes and capacitors placed at the input of the medical device, increases the congestion of the medical device circuits, at least one zener diode and one capacitor per input/output connection or interface. This is contrary to the desire for increased miniaturization of implantable medical devices.

Further, when such protection is provided, interconnect wire length for connecting such protection circuitry and pins of the interfaces to the medical device circuitry that performs desired functions for the medical device tends to be undesirably long. The excessive wire length may lead to signal loss and undesirable inductive effects. The wire length can also act as an antenna that conducts undesirable electrical interference signals to sensitive CMOS circuits within the medical device to be protected.

Additionally, the radio frequency (radio-frequency) energy that is inductively coupled into the wire causes intense heating along the length of the wire, and at the electrodes that are attached to the heart wall. This heating may be sufficient to ablate the interior surface of the blood vessel through which the wire lead is placed, and may be sufficient to cause scarring at the point where the electrodes contact the heart. A further result of this ablation and scarring is that the sensitive node that the electrode is intended to pace with low voltage signals becomes desensitized, so that pacing the patient's heart becomes less reliable, and in some cases fails altogether. Additionally, the switching of the gradient magnetic fields may also induce unwanted voltages causing problems with the circuitry and potential pacing of the heart.

Another conventional solution for protecting the implantable medical device from electromagnetic interference is illustrated in FIG. 1. FIG. 1 is a schematic view of an implantable medical device 12 embodying protection against electrical interference. At least one lead 14 is connected to the implantable medical device 12 in connector block region 13 using an interface.

In the case where implantable medical device 12 is a pacemaker implanted in a body 10, the pacemaker 12 includes at least one or both of pacing and sensing leads represented generally as leads 14 to sense electrical signals attendant to the depolarization and repolarization of the heart 16, and to provide pacing pulses for causing depolarization of cardiac tissue in the vicinity of the distal ends thereof.

FIG. 2 more particularly illustrates the circuit that is used conventionally to protect from electromagnetic interference. As shown in FIG. 2, protection circuitry 15 is provided using a diode array component 30. The diode array consists of five zener diode triggered semiconductor controlled rectifiers (SCRs) with anti-parallel diodes arranged in an array with one common connection. This allows for a small footprint despite the large currents that may be carried through the device during defibrillation, e.g., 10 amps. The SCRs 20-24 turn on and limit the voltage across the device when excessive voltage and current surges occur.

Some of the zener diode triggered SCRs may be connected to an electrically conductive pin, with each electrically conductive pin being connected to a medical device contact region to be wire bonded to pads of a printed circuit board. The diode array component 30 of FIG. 2 may be connected to the electrically conductive pins via die contact regions along with other electrical conductive traces of the printed circuit board.

Other attempts have been made to protect medical assist devices from magnetic-resonance imaging fields. For example, U.S. Pat. No. 5,968,083 (to Ciciarelli et al.) describes a device adapted to switch between low and high impedance modes of operation in response to EMI insult. Furthermore, U.S. Pat. No. 6,188,926 (to Vock) discloses a control unit for adjusting a cardiac pacing rate of a pacing unit to an interference backup rate when heart activity cannot be sensed due to EMI.

Another problem associated with magnetic-resonance imaging is the temperature change in tissue regions caused by using conventional magnetic-resonance imaging techniques. When a substance such as human tissue is subjected to a static magnetic field, the individual magnetic moments of the spins in the tissue align in a parallel and anti-parallel direction with the static magnetic field. This direction along the static magnetic field can be termed as the longitudinal direction. In magnetic-resonance imaging, the radio frequency polarizing field used for spin manipulation is constantly changing and thus, the individual magnetic moments of the spins in the tissue attempt to align with the polarizing field. The constant changing of alignment of the magnetic moments of the spins in the tissue causes the tissue's temperature to increase, thereby exposing the tissue to possible magnetic-resonance imaging induced thermal damage.

Although, conventional medical assist devices provide some means for protection against electromagnetic interference, these conventional medical assist devices require much circuitry and fail to provide fail-safe protection against radiation produced by magnetic-resonance imaging procedures. Moreover, the conventional medical assist devices fail to address the possible damage that can be done at the tissue interface due to radio-frequency-induced heating. Furthermore, the conventional medical assist devices fail to address the unwanted tissue region stimulation that may result from radio-frequency-induced electrical currents. Lastly, conventional magnetic-resonance imaging processes fail to provide a proper safeguard against potential magnetic-resonance imaging induced thermal damage due to the tissue's exposure to the switching magnetic field gradients and the circularly polarized Radio Frequency Field of the magnetic-resonance imaging process.

Thus, it is desirable to provide protection against electromagnetic interference, without requiring much circuitry and to provide fail-safe protection against radiation produced by magnetic-resonance imaging procedures. Moreover, it is desirable to provide medical assist devices that prevent the possible tissue damage that can be done at the tissue interface due to induced electrical signals. Furthermore, it is desirable to provide an effective means for transferring energy from one point in the body to another point without having the energy causing a detrimental effect upon the body. Lastly, it is desirable to implement a magnetic-resonance imaging process, which can be modified, automatically or manually, in response to sensed tissue temperature changes or known localized specific energy absorption rates, so as to prevent possible magnetic-resonance imaging induced thermal damage.

SUMMARY OF THE PRESENT INVENTION

A first aspect of the present invention is directed to a medical assist system. The medical assist system includes a primary device housing, the primary device housing having a control circuit therein; a lead system to provide an electrical path between a tissue region and the primary device housing; and a shielding formed around the lead system to shield the lead system from electromagnetic interference. The shielding is patterned with non-conductive materials and conductive material.

A second aspect of the present invention is directed to a medical assist device. The medical assist device includes a primary device housing, the primary device housing having a control circuit therein, and a shielding formed around the primary device housing to shield the primary device housing and any circuits therein from electromagnetic interference. The shielding is patterned with non-conductive materials and conductive material.

A third aspect of the present invention is directed to an electromagnetic shielded implantable lead. The electromagnetic shielded implantable lead includes an electrical lead and a shielding formed around the electrical lead to shield the electrical lead from electromagnetic interference. The shielding is patterned with non-conductive materials and conductive material.

A fourth aspect of the present invention is directed to an electromagnetic shield. The electromagnetic shield includes a first patterned layer having non-conductive materials and conductive material and a second patterned layer having non-conductive materials and conductive material.

A fifth aspect of the present invention is a magnetic-resonance imaging process. The magnetic-resonance imaging process images a tissue region according to an image acquisition sequence and adjusts the image acquisition sequence, in response to a predetermined parameter, to allow for cooling of the imaged tissue region.

A sixth aspect of the present invention is a magnetic-resonance imaging process. The magnetic-resonance imaging process images a tissue region according to an image acquisition sequence; adjusts the image acquisition sequence, in response to a predetermined parameter, to allow for cooling of the imaged tissue region; and shields components of a medical assist device with a shield patterned with non-conductive materials and conductive material.

A seventh aspect of the present invention is a device for amplifying an electrical signal of physiological significance in a magnetic-resonance imaging environment. The device includes at least two electrodes with associated input leads for coupling to a patient; an amplifier having a zero-signal reference terminal for detecting and amplifying the desired physiological signal; and a filter, connected to the input leads and coupling the at least two electrodes to the amplifier, to attenuate any induced radio-frequency signal produced in the magnetic-resonance imaging environment and passing the lower frequency desired electrical physiological signal. The filter includes a shield enclosing the filter. The shield enclosing the filter is patterned with non-conductive materials and conductive material.

An eighth aspect of the present invention is a medical assist system. The medical assist device includes a primary device housing; the primary device housing having a control circuit therein; a lead system to provide an electrical path between a tissue region and the primary device housing; a shielding formed around the lead system to shield the lead system from electromagnetic interference; and a filter, connected to the lead system, to attenuate any induced radio-frequency signal and passing a desired electrical physiological signal. The filter includes a shield enclosing the filter and a low pass filter connected to the lead system. The shielding is patterned with non-conductive materials and conductive material.

A ninth aspect of the present invention is a medical assist system. The medical assist system includes a primary device housing, the primary device housing having a control circuit therein; a lead system to provide an electrical path between a tissue region and the primary device housing; and a shielding formed around the lead system to shield the lead system from electromagnetic interference. The shielding is an apertured conductive material having a maximum aperture dimension of 0.01 millimeters to 10 millimeters.

A tenth aspect of the present invention is a medical assist device. The medical assist device includes a primary device housing, the primary device housing having a control circuit therein; and a shielding formed around the primary device housing to shield the primary device housing and any circuits therein from electromagnetic interference. The shielding is an apertured conductive material having a maximum aperture dimension of 0.01 millimeters to 10 millimeters.

An eleventh aspect of the present invention is an electromagnetic shielded lead. The electromagnetic shielded lead includes an electrical lead and a shielding formed around the electrical lead to shield the electrical lead from electromagnetic interference. The shielding is an apertured conductive material having a maximum aperture dimension of 0.01 millimeters to 10 millimeters.

A twelfth aspect of the present invention is an electromagnetic shield. The electromagnetic shield includes a first apertured conductive material having a maximum aperture dimension of 0.01 millimeters to 10 millimeters and a second apertured conductive material having a maximum aperture dimension of 0.01 millimeters to 10 millimeters.

A further aspect of the present invention is a magnetic-resonance imaging process. The magnetic-resonance imaging process images a tissue region according to an image acquisition sequence; adjusts the image acquisition sequence, in response to a predetermined parameter, to allow for cooling of the imaged tissue region; and shields components of a medical assist device with a shield being an apertured conductive material and having a maximum aperture dimension of 0.01 millimeters to 10 millimeters.

A still further aspect of the present invention is a device for amplifying an electrical signal of physiological significance in a magnetic-resonance imaging environment. The device includes at least two electrodes with associated input leads for coupling to a patient; an amplifier having a zero-signal reference terminal for detecting and amplifying the desired physiological signal; and a filter, connected to the input leads and coupling the at least two electrodes to the amplifier, to attenuate any induced RF signal produced in the magnetic-resonance imaging environment and passing the lower frequency desired electrical physiological signal. The filter includes a shield enclosing the filter. The shield is an apertured conductive material having a maximum aperture dimension of 0.01 millimeters to 10 millimeters.

Another aspect of the present invention is a medical assist system. The medical assist system includes a primary device housing, the primary device housing having a control circuit therein; a lead system to provide an electrical path between a tissue region and the primary device housing; a shielding formed around the lead system to shield the lead system from electromagnetic interference; and a filter, connected to the lead system, to attenuate any induced RF signal and passing a desired electrical physiological signal. The filter includes a shield enclosing the filter and a low pass filter connected to the lead system. The shielding is an apertured conductive material having a maximum aperture dimension of 0.01 millimeters to 10 millimeters.

BRIEFS DESCRIPTION OF THE DRAWINGS

The present invention may take form in various components and arrangements of components, and in various steps and arrangements of steps. The drawings are only for purposes of illustrating a preferred embodiment and are not to be construed as limiting the present invention, wherein.

Figure 35:
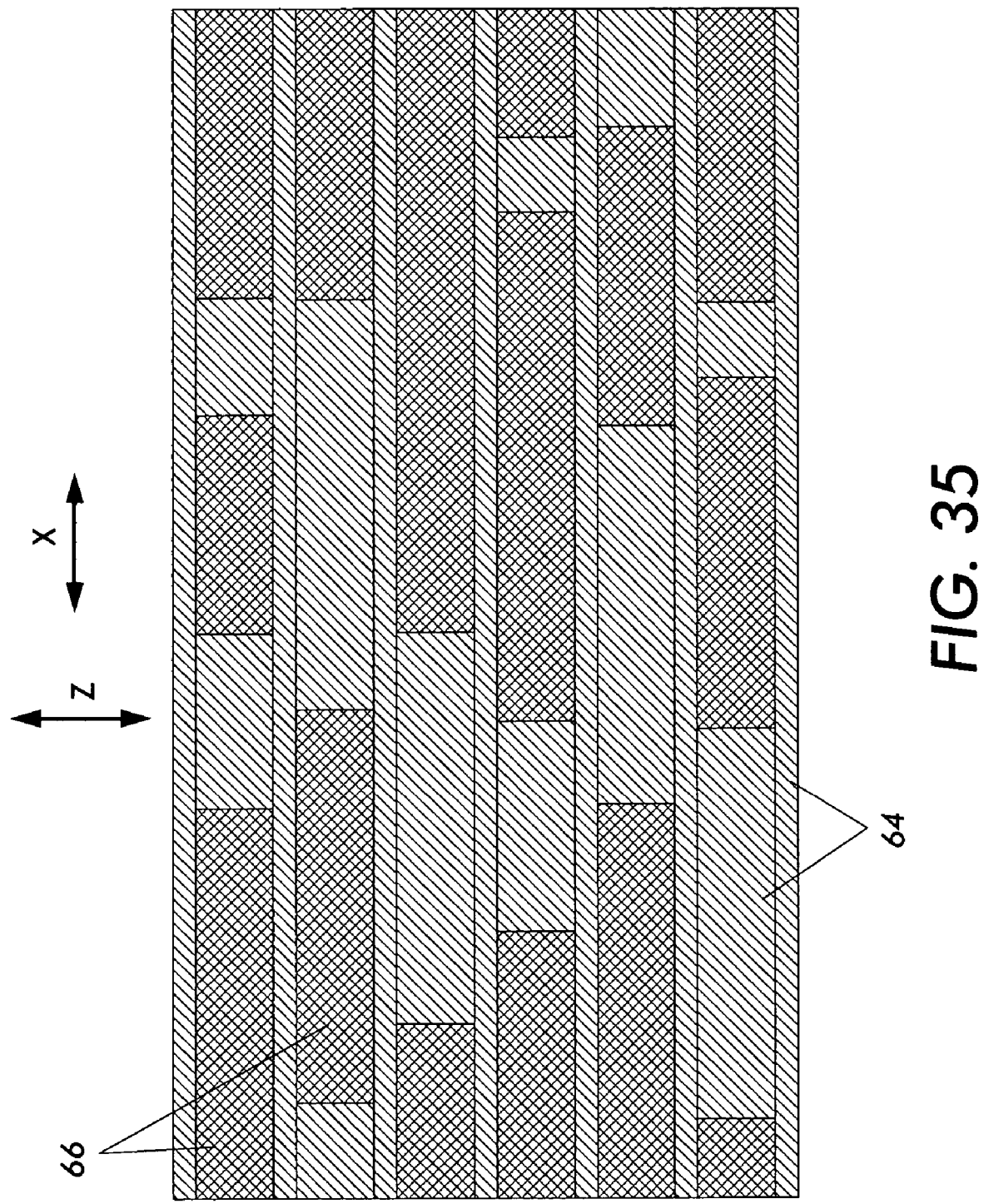
Figure 36:
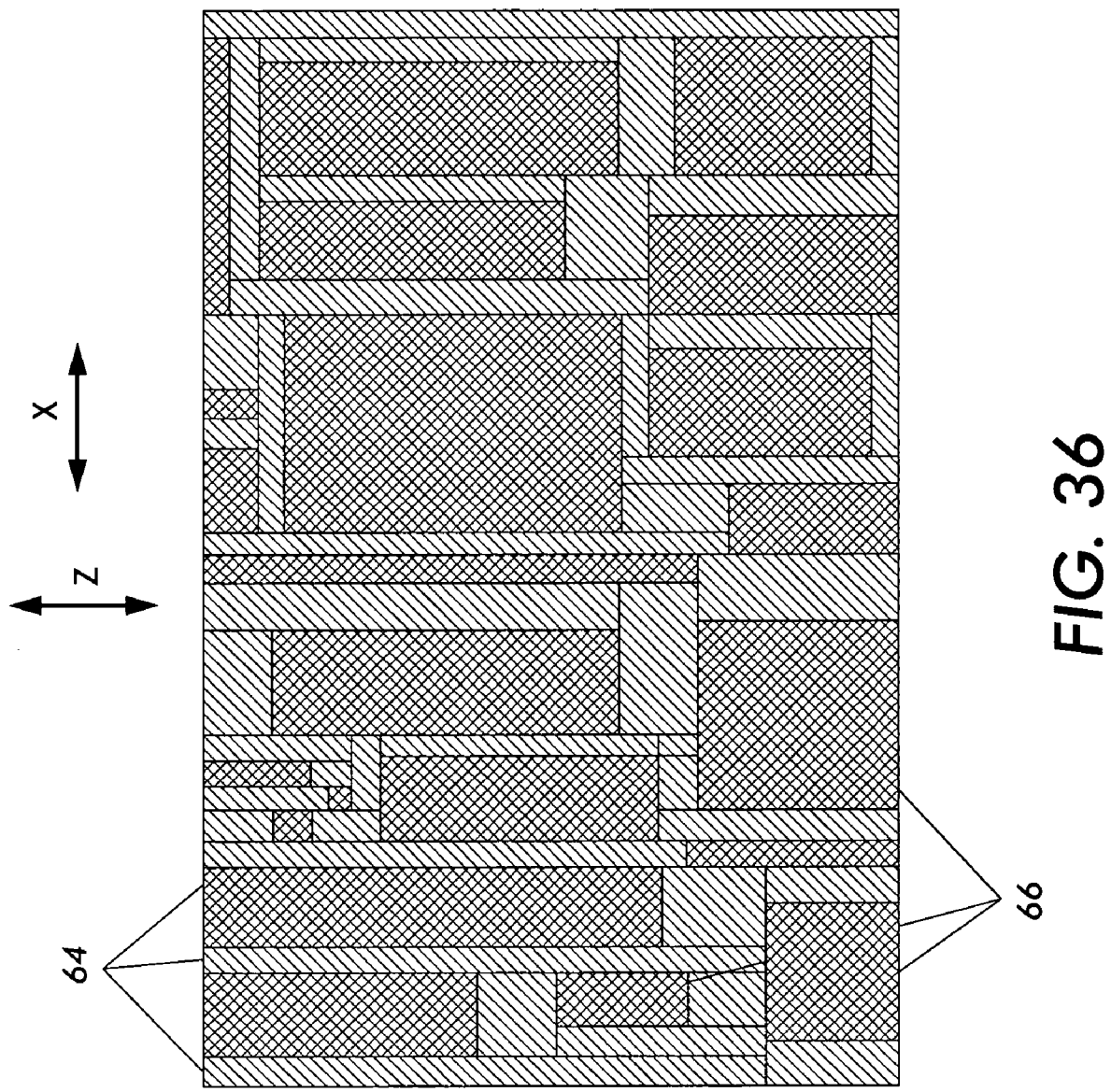

FIG. 35 is a top view of a layer of another embodiment of the apertured shielding, having a predetermined apertured pattern of non-conductive materials, for a wire lead according to the concepts of the present invention; and FIG. 36 is a top view of a layer of another embodiment of the apertured shielding, having a random apertured pattern of non-conductive materials, for a wire lead according to the concepts of the present invention.

DETAILED DESCRIPTION OF THE PRESENT INVENTION

As noted above, the present invention is directed to an implantable device, such as a medical assist device, that is immune or hardened to electromagnetic insult or interference.

For a general understanding of the present invention, reference is made to the drawings. In the drawings, like reference have been used throughout to designate identical elements. In describing the present invention, the following term(s) have been used in the description.

For the purposes of the description below and the appended claims, the term, medical assist device/system or tissue invasive device/system, refers to any device/system that may enable monitoring of living tissue(s) or living, system(s) wherein the monitoring may be, but not limited to an EKG signal, an ECG signal, a glucose level, hormone level, cholesterol level, or magnetic resonance image. The medical assist device/system or tissue invasive device/system may also enable stimulus intervention to provide assistance to living tissue(s) or living system(s) so that the stimulus causes the selected body tissue or system to function as desired. The stimulus may be, but not limited to, a cardiac stimulating substance or electrical pulse, a blood thinning substance, insulin, estrogen, progesterone, or testosterone.

The medical assist device/system or tissue invasive device/system may also provide therapeutic treatment to the living tissue(s) or living system(s) so that the treatment causes the selected body tissue or system to function as desired. The stimulus may be, but not limited to, radio frequency or laser ablation.

Furthermore, the medical assist device/system or tissue invasive device/system may be implanted in a body cavity of a living organism, either temporarily or permanently, or subcutaneously implanted into a living organism either temporarily or permanently. Moreover, the medical assist device/system or tissue invasive device/system may be located external to the living organism. Examples of medical assist devices/systems or tissue invasive devices/systems are, but not limited to, wearable or implantable cardiac pacers (such as pacemakers), implantable pulse generators (IPGs), cardioverter/defibrillator/pacemakers (CDPs), cardiac monitoring systems, insulin pump controllers, brain monitoring systems, cardiac assist devices, implanted insulin pumps, catheter guide wires, leads for neurostimulation probes, intraluminal coils, guided catheters, temporary cardiac pacemakers, temporary esophageal pacemakers, etc.

Although the thrust of the description of one embodiment of the present invention, below, will use a cardiac assist system as an example of the workings of the concepts of the present invention, the concepts are directed to any medical assist device/system, tissue invasive device/system or tissue interactive device/system which includes electrical components that require shielding from electromagnetic interference or insult such that the interference or insult could cause damage to the electrical components or damage to the surrounding tissue.

As noted above, a typical medical device may be a pacemaker. The pacemaker may include at least one or both of pacing and sensing leads represented generally as leads to sense electrical signals attendant to the depolarization and repolarization of the heart and to provide pacing pulses for causing depolarization of cardiac tissue in the vicinity of the distal ends thereof.

The pacemaker or cardiac assist device may include a primary device housing. The primary device housing may include a control circuit, such as a microprocessor integrated circuit for controlling the operations of the cardiac assist system. The control circuit may select a mode of operation for the cardiac assist system based on predetermined sensed parameters. The primary device housing may also include circuitry to detect and isolate cross talk between device pulsing operations and device sensing operations. The control circuit may isolate physiological signals using a noise filtering circuit or a digital noise filtering.

The control circuit can be programmable from a source external of the primary device housing or the control circuit can provide physiological diagnostics to a source external of the primary device housing.

The primary device housing may include a power source. The power source may be a battery power source in combination with a battery power source measuring circuit. Further, the control circuit may automatically adjust a value for determining an elective replacement indication condition of a battery power source such that the value is automatically adjusted by the control circuit in response to a measured level of a state of the battery power source, the measured level generated by the battery power source measuring circuit connected to the battery power source.

As noted above, both the primary housing and the leads of the medical assist device/system require protection or shielding from electromagnetic interference or insult. The present invention provides a shielding that substantially prevents electromagnetic interference from damaging any, contained therein, electrical components or damage to the tissue surrounding the medical assist device/system's primary housing or leads. The shielding is a compilation of patterned layers having non-conductive materials and conductive materials contained in each patterned layer.

As is known is well known, conductive material provides a shield or block for electromagnetic radiation, especially radio frequency radiation ("radio-frequency") or magnetic radiation ("magnetic-resonance imaging") used in magnetic-resonance imaging so that the magnetic-resonance imaging radiation cannot penetrate the conductive materials to do damage to any electrical components located on the other side of the shield.

However, although conductive material may provide a block to the magnetic-resonance imaging radiation so as to prevent penetration of the magnetic-resonance imaging radiation, the blocking of the magnetic-resonance imaging radiation can cause eddy currents to be induced in the conductive material by the changing magnetic fields in the magnetic-resonance imaging radiation. The eddy currents may cause heating of the conductive material, thereby heating the enclosed electrical components so as to cause damage or heating the surrounding tissue so as to cause tissue damage.

To prevent the eddy currents from being induced to a level, which may cause damage from excessive heat, the conductive material in the shielding of the present invention is patterned, apertured, or segmented. More specifically, magnetic-resonance imaging radiation shields generally contain thin layers of conductive cladding sometimes separated by insulators or dielectrics. In the present invention, the conductive material in a layer is patterned, apertured, or segmented so that the conductive material is literally broken up to limit the build up of eddy currents induced by the changing magnetic fields produced during magnetic-resonance imaging.

Figure 1:
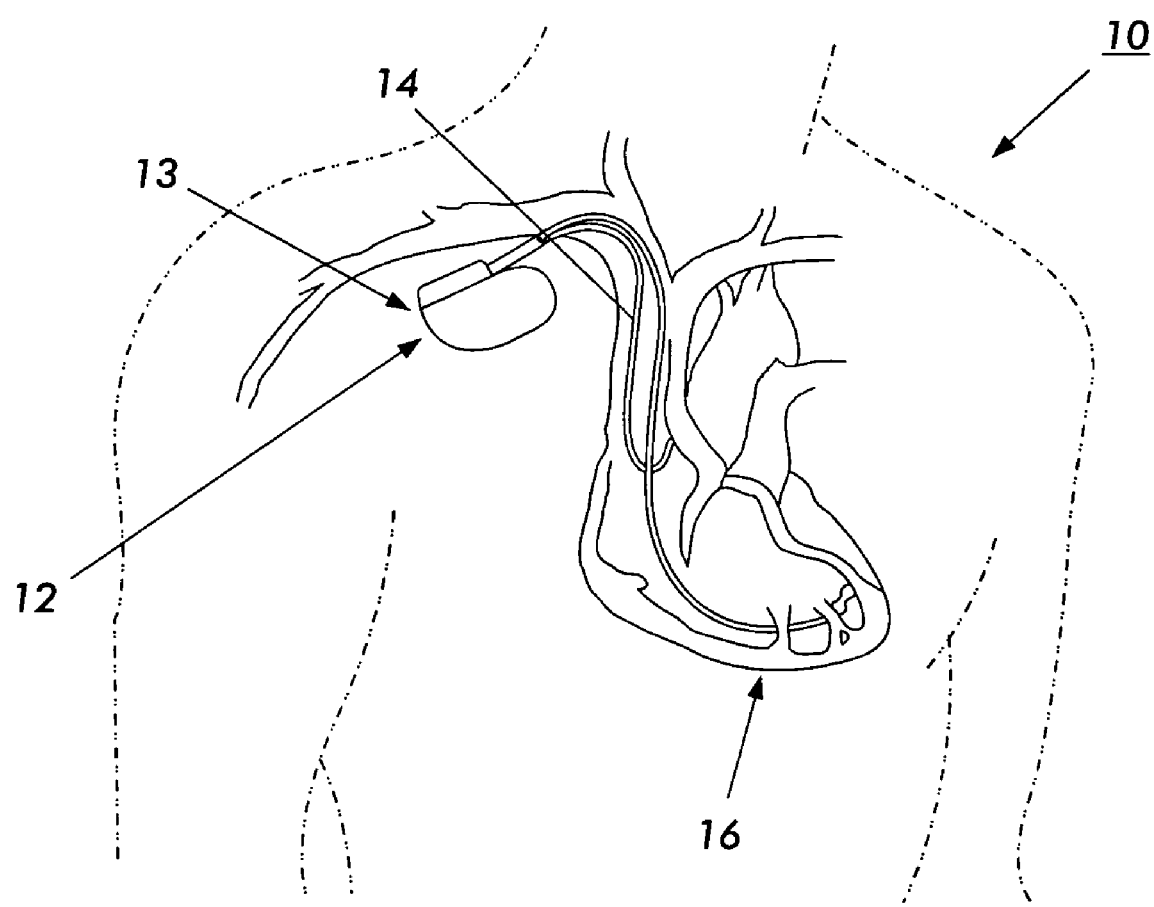
FIGS. 1 and 2 are illustrations of conventional techniques used to protect against electromagnetic interference.
Figure 2:
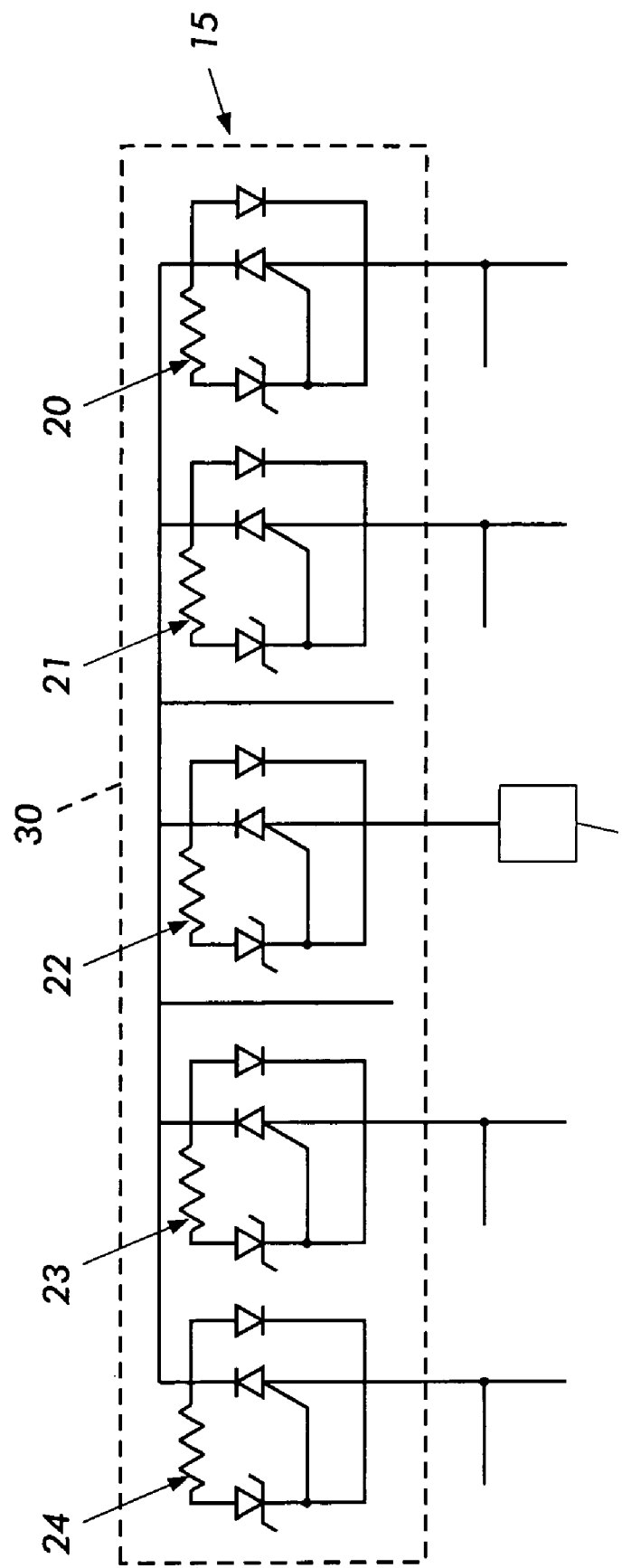
Figure 3:
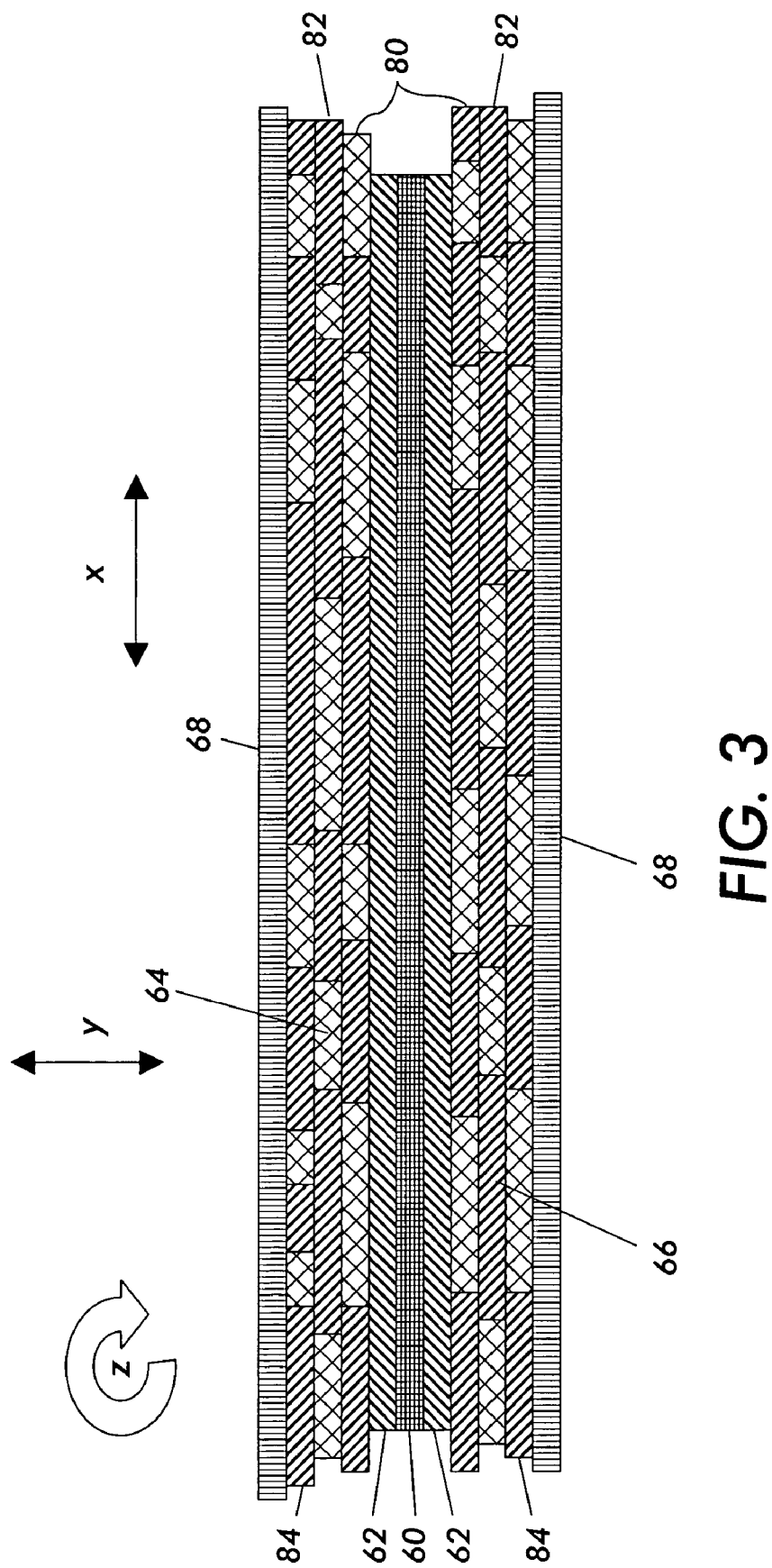
FIG. 3 is a cross-sectional view of one embodiment of segmented shielding of a wire lead according to the concepts of the present invention.

An example of such a patterned or segmented shielding for use with an electrical lead is illustrated in FIG. 3. As shown in FIG. 3, an electrical lead 60 is initially coated with an insulation layer 62 so as to electrically insulate the electrical lead from its surroundings. Upon the insulation layer 62, a first patterned or segmented layer 80 of shielding is placed or formed thereon. The first patterned or segmented layer 80 includes conductive materials 64 and non-conductive material(s) 66.

Upon the first patterned or segmented layer 80 of shielding, a second patterned or segmented layer 82 of shielding is placed or formed thereon. The second patterned or segmented layer 82 includes conductive materials 64 and non-conductive material(s) 66.

It is noted that the non-conductive material 66 may be formed of a single integral piece of non-conductive material or be formed from a multitude of pieces of non-conductive material, the multitude of pieces being connected together in such a manner to function as a single integral piece of non-conductive material.

Upon the second patterned or segmented layer 82 of shielding, a third patterned or segmented layer 84 of shielding is placed or formed thereon. The third patterned or segmented layer 84 includes conductive materials 64 and non-conductive material(s) 66.

The conductive materials 64 of this embodiment of the present invention may be a metal, a carbon composite, nanotubes (wherein the nanotubes may be constructed from a carbon base or the nanotubes could be formed from other amalgams coated with the appropriate material(s)), metal-coated carbon filaments (wherein the metal may be one of the following metals: nickel, copper, cobalt, silver, gold, tin, or zinc), metal-coated ceramic filaments (wherein the metal may be one of the following metals: nickel, copper, cobalt, silver, gold, tin, or zinc), a composite of metal-coated carbon filaments and a polymer (wherein the polymer may be one of the following: polyether sulfone, silicone, polymide, polyvinylidene fluoride, or epoxy), a composite of metal-coated ceramic filaments and a polymer (wherein the polymer may be one of the following: polyether sulfone, silicone, polymide, polyvinylidene fluoride, or epoxy), a composite of metal-coated carbon filaments and a ceramic (wherein the ceramic may be one of the following: cement, silicates, phosphates, silicon carbide, silicon nitride, aluminum nitride, or titanium diboride), a composite of metal-coated ceramic filaments and a ceramic (wherein the ceramic may be one of the following: cement, silicates, phosphates, silicon carbide, silicon nitride, aluminum nitride, or titanium diboride), or a composite of metal-coated (carbon or ceramic) filaments (wherein the metal may be one of the following metals: nickel, copper, cobalt, silver, gold, tin, or zinc) and a polymer/ceramic combination (wherein the polymer may be one of the following: polyether sulfone, silicone, polymide, polyvinylidene fluoride, or epoxy and the ceramic may be one of the following: cement, silicates, phosphates, silicon carbide, silicon nitride, aluminum nitride, or titanium diboride).

A more detailed description of the coated filaments is found in U.S. Pat. No. 5,827,997, entitled "Metal Filaments for Electromagnetic Interference Shielding." The entire content of U.S. Pat. No. 5,827,997 is hereby incorporated by reference.

The non-conductive material(s) 66 of this embodiment of the present invention may be a ceramic; glass; mica; anodized copper; metallic oxides; natural or synthetic rubbers; or resins, such as natural resins, epoxy resins, or silicones.

Over the shielding, a biocompatible layer 68 may be placed or formed thereon. Preferably, the biocompatible layer is a non-permeable diffusion resistant biocompatible material.

As illustrated in FIG. 3, the conductive materials 64 are segmented or patterned in an x-direction, wherein the x-direction is a direction substantially parallel to an axis of the lead 60. In other words, the conductive materials 64 are broken up in this direction such that one conductive material 64 is physically separated from a neighboring conductive material 64 in the same layer.

Moreover, as illustrated in FIG. 3, the conductive materials 64 of different layers are segmented or patterned in a y-direction, wherein the y-direction is a direction substantially perpendicular to an axis of the lead 60. In other words, the conductive materials 64 of different layers are broken up in this direction such that one conductive material 64 is electrically isolated from a neighboring conductive material 64 in an immediate adjacent layer; i.e., a conductive material 64 in the first patterned or segmented layer 80 is electrically isolated from a neighboring conductive material 64 in the second patterned or segmented layer 82.

Preferably, the x-directional gap between non co-layer immediately x-directional adjacent conductive materials 64 is much smaller than the wavelength of the electromagnetic pulse that the shield must attenuate to prevent the incident pulse from passing unattenuated through the shield.

Lastly, the conductive materials 64 may be segmented or patterned in a z-direction, wherein the z-direction represents the planar surface of a layer as it is wrapped around the lead 60.

Figure 4:
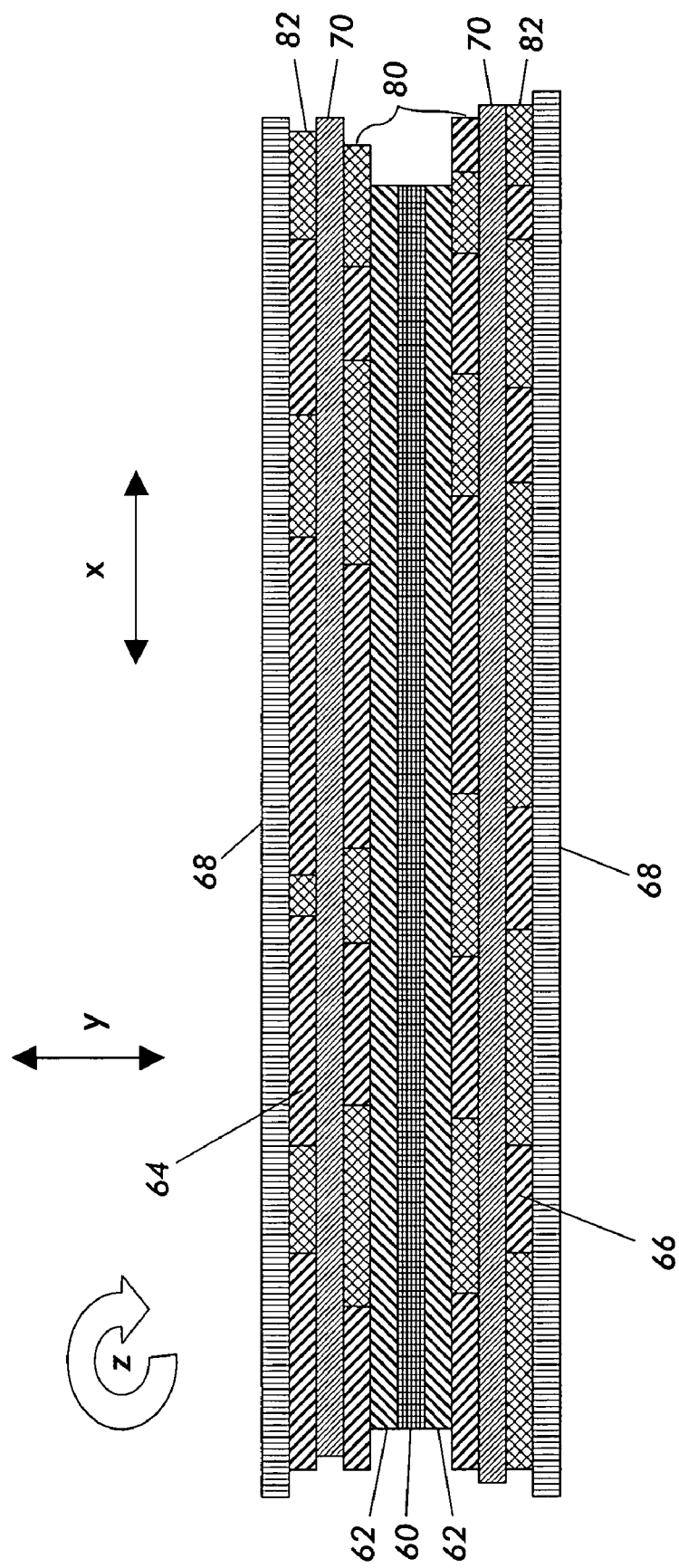
FIG. 4 is a cross-sectional view of another embodiment of segmented shielding of a wire lead according to the concepts of the present invention.

Another example of such a patterned or segmented shielding for use with an electrical lead is illustrated in FIG. 4. As shown in FIG. 4, an electrical lead 60 is initially coated with an insulation layer 62 so as to electrically insulate the electrical lead from its surroundings. Upon the insulation layer 62, a first patterned or segmented layer 80 of shielding is placed or formed thereon. The first patterned or segmented layer 80 includes conductive materials 64 and non-conductive material(s) 66.

As noted above, the non-conductive material 66 may be formed of a single integral piece of non-conductive material or be formed from a multitude of pieces of non-conductive material, the multitude of pieces being connected together in such a manner to function as a single integral piece of non-conductive material.

Upon the first patterned or segmented layer 80 of shielding, a layer 70 of non-conductive material is placed or formed thereon. Upon the layer 70 of non-conductive material, a second patterned or segmented layer 82 of shielding is placed or formed thereon. The second patterned or segmented layer 82 includes conductive materials 64 and non-conductive material(s) 66.

The conductive materials 64 of this embodiment of the present invention may be a metal, a carbon composite, nanotubes (wherein the nanotubes may be constructed from a carbon base or the nanotubes could be formed from other amalgams coated with the appropriate material(s)), metal-coated carbon filaments (wherein the metal may be one of the following metals: nickel, copper, cobalt, silver, gold, tin, or zinc), metal-coated ceramic filaments (wherein the metal may be one of the following metals: nickel, copper, cobalt, silver, gold, tin, or zinc), a composite of metal-coated carbon filaments and a polymer (wherein the polymer may be one of the following: polyether sulfone, silicone, polymide, polyvinylidene fluoride, or epoxy), a composite of metal-coated ceramic filaments and a polymer (wherein the polymer may be one of the following: polyether sulfone, silicone, polymide, polyvinylidene fluoride, or epoxy), a composite of metal-coated carbon filaments and a ceramic (wherein the ceramic may be one of the following: cement, silicates, phosphates, silicon carbide, silicon nitride, aluminum nitride, or titanium diboride), a composite of metal-coated ceramic filaments and a ceramic (wherein the ceramic may be one of the following: cement, silicates, phosphates, silicon carbide, silicon nitride, aluminum nitride, or titanium diboride), or a composite of metal-coated (carbon or ceramic) filaments (wherein the metal may be one of the following metals: nickel, copper, cobalt, silver, gold, tin, or zinc) and a polymer/ceramic combination (wherein the polymer may be one of the following: polyether sulfone, silicone, polymide, polyvinylidene fluoride, or epoxy and the ceramic may be one of the following: cement, silicates, phosphates, silicon carbide, silicon nitride, aluminum nitride, or titanium diboride).

Over the shielding, a biocompatible layer 68 may be placed or formed thereon. Preferably, the biocdmpatible layer is a non-permeable diffusion resistant biocompatible material.

The non-conductive materials 66 of this embodiment of the present invention may be a ceramic; glass; mica; anodized copper; metallic oxides; natural or synthetic rubbers; or resins, such as natural resins, epoxy resins, or silicones.

As illustrated in FIG. 4, the conductive materials 64 are segmented or patterned in an x-direction, wherein the x-direction is a direction substantially parallel to an axis of the lead 60. In other words, the conductive materials 64 are broken up in this direction.

Moreover, as illustrated in FIG. 4, the conductive materials 64 are patterned or segmented in a y-direction, wherein the y-direction is a direction substantially perpendicular to an axis of the lead 60. In other words, the conductive materials 64 are broken up in this direction such that one conductive material 64 is electrically isolated from a neighboring conductive material 64 in an immediate adjacent layer; i.e., a conductive material 64 in the first patterned or segmented layer 80 is electrically isolated from a neighboring conductive material 64 in the second patterned or segmented layer 82.

Preferably, the x-directional gap between non co-layer immediately x-directional adjacent conductive materials 64 is much smaller than the wavelength of the electromagnetic pulse that the shield must attenuate to prevent the incident pulse from passing unattenuated through the shield.

Lastly, the conductive materials 64 may be segmented in a z-direction, wherein the z-direction represents the planar surface of a layer as it is wrapped around the lead 60.

As noted above, the conductive material 64 is patterned or segmented to limit the build up of eddy currents. Examples of the patterning of the conductive materials 64 are illustrated in FIGS. 5-7.

Figure 5:
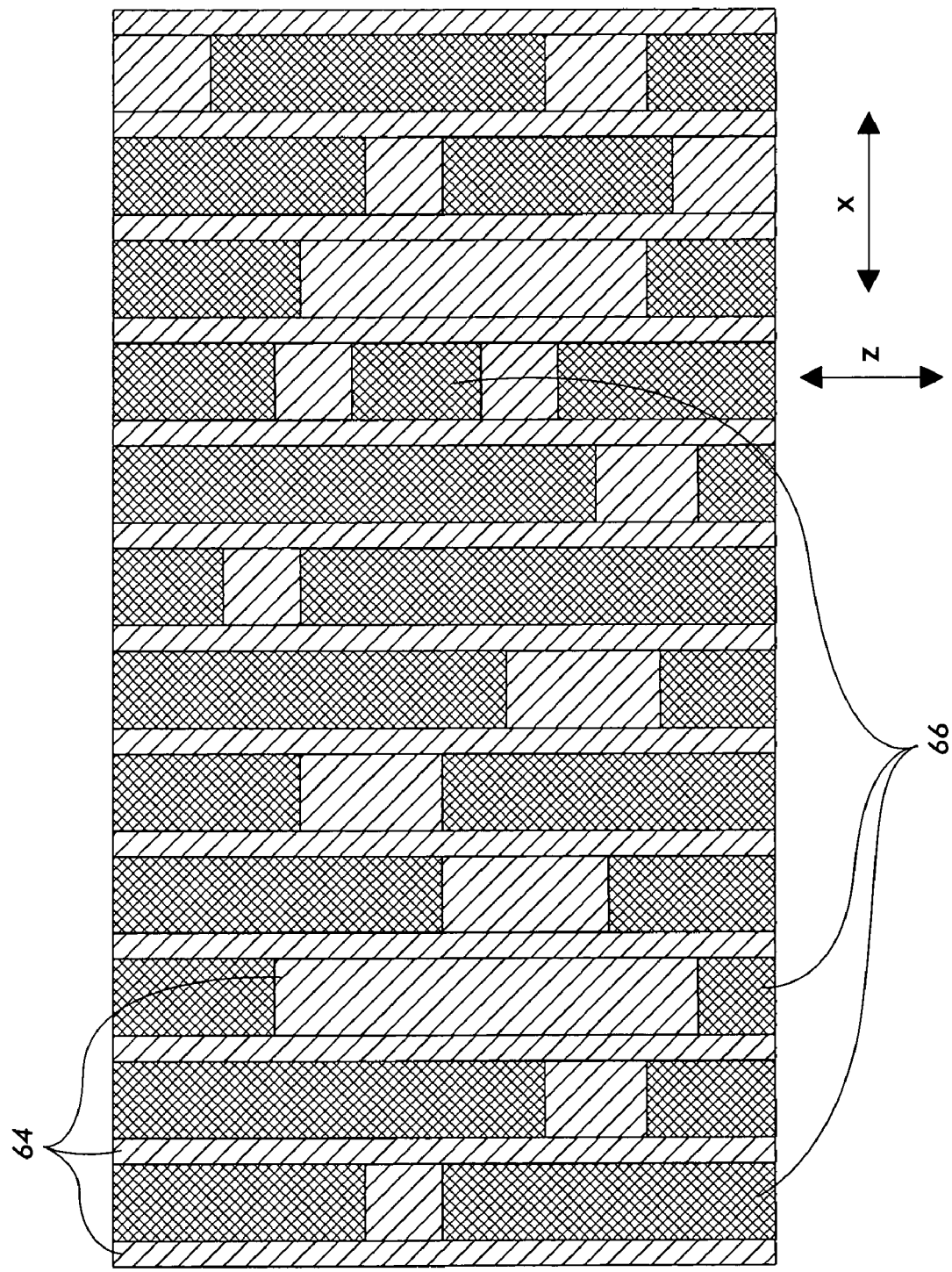
FIG. 5 is a top view of a layer of an embodiment of the shielding, having a predetermined segmented pattern of conductive materials, for a wire lead shielding according to the concepts of the present invention.

FIG. 5 illustrated a top view of a fabricated layer of the shielding. As illustrated in FIG. 5, the conductive materials 64 are patterned or segmented in such a way that a width of the conductive material 64 in the x-direction, the x-direction being substantially parallel to an axis of a lead, is substantially equal. More specifically, the conductive materials 64 is patterned or segmented in such a way that conductive materials 64 spaced in a predetermined manner; e.g., the spacing between the conductive materials 64, in the x-direction, may be equal or set in a predetermined manner. Lastly, the spacing between conductive materials 64 in a z-direction, the z-direction representing the planar surface of a layer as it is wrapped around a lead, is not necessarily equal or set in a predetermined manner; however the spacing in the z-direction may be equal or set in a predetermined manner.

Figure 6:
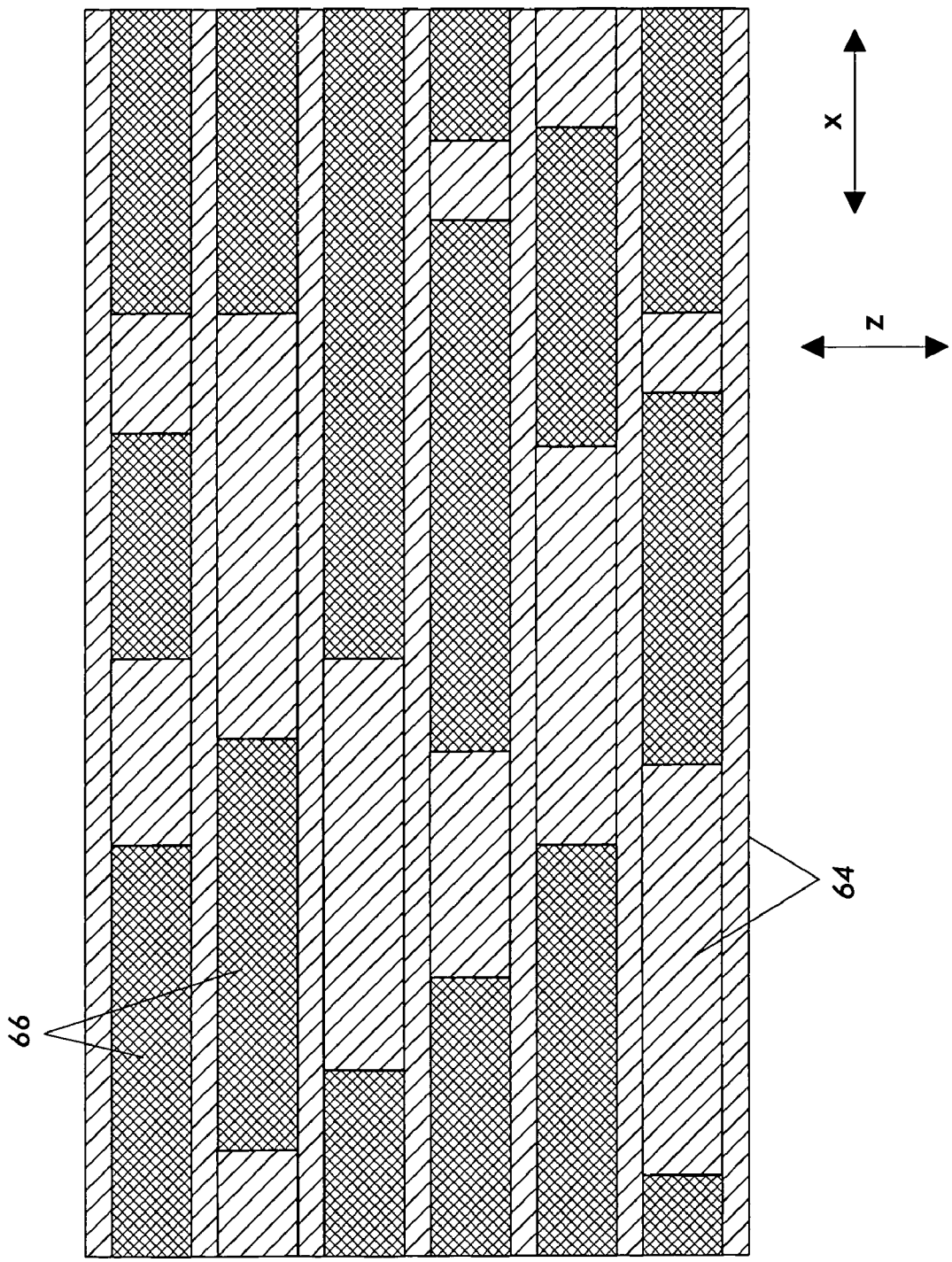
FIG. 6 is a top view of a layer of another embodiment of the shielding, having a predetermined segmented pattern of conductive materials, for a wire lead according to the concepts of the present invention.

FIG. 6 illustrated a top view of a fabricated layer of the shielding. As illustrated in FIG. 6, the conductive materials 64 are patterned or segmented in such a way that a width of the conductive material 64 in the z-direction, the z-direction representing the planar surface of a layer as it is wrapped around a lead, is substantially equal. More specifically, the conductive materials 64 are patterned or segmented in such a way that conductive materials 64 spaced in a predetermined manner; e.g., the spacing between the conductive materials 64, in the z-direction, may be equal or set in a predetermined manner. Lastly, the spacing between conductive materials 64 in a x-direction, the x-direction being substantially parallel to an axis of a lead, is not necessarily equal or set in a predetermined manner; however the spacing in the x-direction may be equal or set in a predetermined manner.

Figure 7:
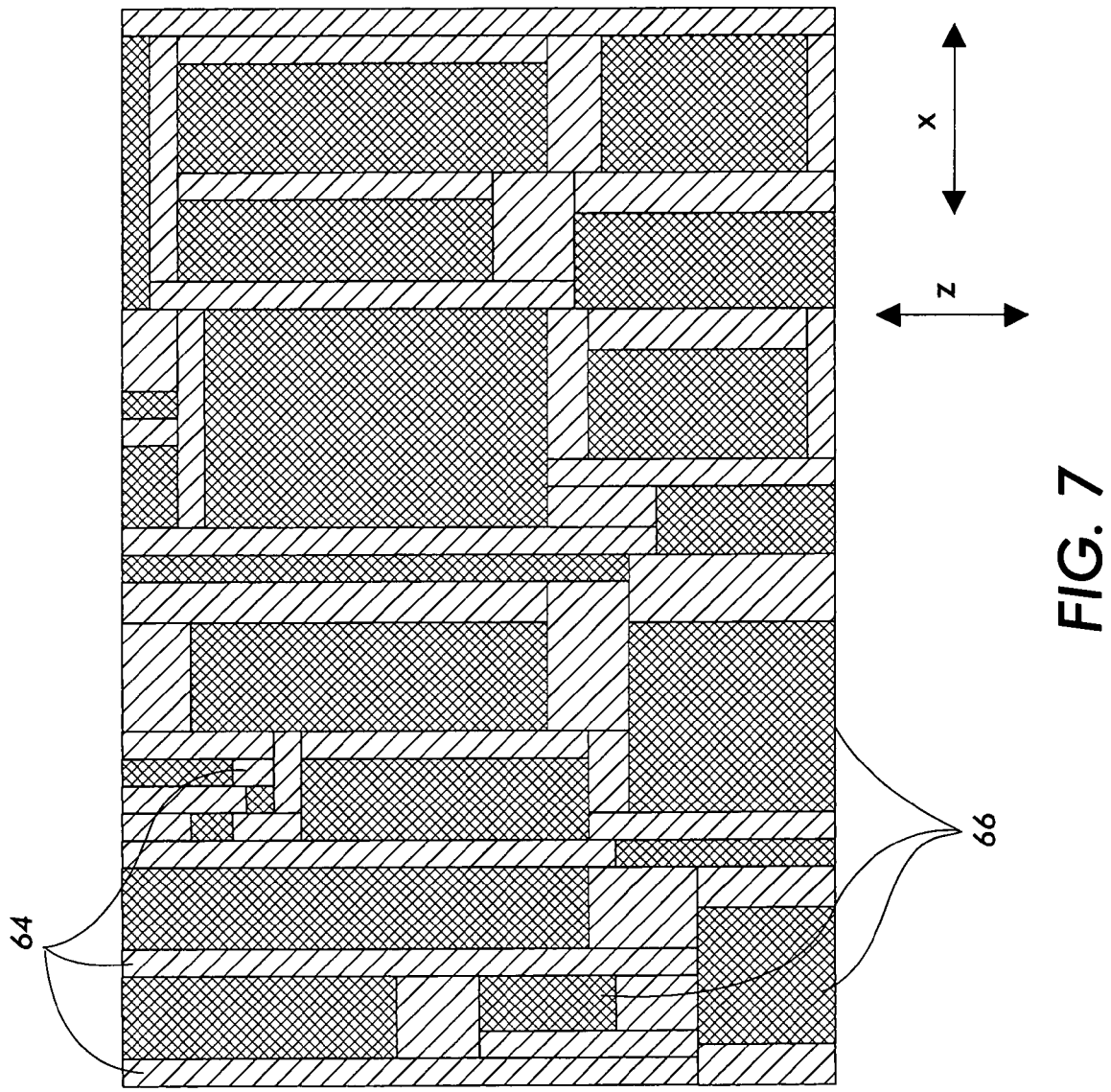
FIG. 7 is a top view of a layer of another embodiment of the shielding, having a random pattern of conductive materials, for a wire lead according to the concepts of the present invention.

FIG. 7 illustrated a top view of a fabricated layer of the shielding. As illustrated in FIG. 7, the conductive material 64 are patterned or segmented in such a way that the widths of the conductive materials 64 in the z-direction, the z-direction representing the planar surface of a layer as it is wrapped around a lead, are random. More specifically, the conductive materials 64 are patterned or segmented in such a way that conductive materials 64 are spaced in a random manner. Lastly, the spacing between conductive materials 64 in an x-direction, the x-direction being substantially parallel to an axis of a lead, is also random.

It is noted that the although FIGS. 3-7 show a shielding with respect to a lead, the shielding can be used to shield other shaped devices such as electrical component housings or other components of a medical assist device/system.

It is further noted that the actual dimensions of the non-conductive materials can be set to suppress the radiation and eddy currents induced from specific frequencies; e.g., the lengths of the non-conductive material can be varied to suppress or block specific or undesired radiation frequencies. The dimensions of the non-conductive material would be on the order of the wavelength of the radiation so as to suppress, block, or shield the radiation.

The actual layers may be formed using a photoresist/masking process such as used in integrated circuit fabrication and thin film deposition. By using a mask/photoresist process, the conductive/insulative layers in the vertical direction can be easily formed so that the conductive/insulative layers alternate (radially outward from the axis of the lead), and the conductive/insulative layers in the horizontal direction also alternate (substantially parallel to an axis of the lead).

As noted above, the shielding may also be apertured. More specifically, implantable medical devices, such as pacemaker leads, typically demonstrate heating of 10-100° C., whereas body tissues can be irreversibly damaged by increases in temperature of as little as 2-4° C. Therefore, up to a 50× reduction in the amount of energy delivered to the implanted medical device is required to make the device safe, 100× if a reasonable design margin of safety is desired. This reduction in the amount of energy delivered to the implanted medical device corresponds to 20 dB of attenuation.

The performance of a shield or shield effectiveness (SE) with a circular opening has been shown to be:

$$SE(dB) = 20 \log[\lambda/2\pi r]$$

where $\lambda$ is the incident wavelength and r is the radius of the circular opening.

For holes of other shapes (e.g. an annulus) the factor $2\pi r$ may be replaced by 2 L where L is the largest dimension of the opening (i.e. the circumference):

$$SE(dB) = 20 \log[\lambda/2L]$$

This formula indicates that a slot or annulus with a greatest dimension equal to 1/20 of the wavelength is required to provide a shielding effectiveness (SE) against heating effects of 20 dB.

The wavelength at a particular frequency in air is given by the equation $\lambda = c/f$, where c is the speed of light ($3 \times 10^8$ meters/second) and f is the frequency. However, the wavelength in a particular material, such as body tissues, is given by the following equation:

$$\lambda_m = \lambda_o/[\epsilon_{rel}]^{1/2}$$

where $\epsilon_{rel}$ is the relative dielectric constant.

At a frequency of 64 MHz and $\epsilon_{rel} = 80$ (a typical value for body tissue), $\lambda_o$ is equal to 4.7 meters, and $\lambda_m$ is equal to 0.5 meters. At a frequency of 64 MHz, a shield effectiveness of 20 dB requires that L, the maximum aperture dimension (i.e. annulus circumference), not exceed 0.025 meters or 25 millimeters (L=0.5 meters/20).

However, it is well known that shielding effectiveness is reduced as the number of openings N is increased. Shield effectiveness scales as the square root on N.

In the present invention, N may range from 10 to 1000. Therefore, to maintain minimum shield effectiveness against heating effects of 20 dB, the maximum aperture dimension should not exceed approximately 10 millimeters to 1 millimeter, depending upon how many apertures or openings are incorporated into the shield design. At higher frequencies such as 128 MHz (the frequency of emerging MRI facilities), the maximum aperture dimension should not exceed 5 millimeters to 0.5 millimeters.

Moreover, implantable medical devices, such as pacemaker leads, must also be capable of making sensitive electrical measurements such as intracardiac ECG signals, which are typically 1-25 millivolts. To insure the accurate measurements of such signals, a measurement resolution capability of less than 0.1 millivolt is required. Experimental measurements have shown that MRI procedures can induce voltages of as much as 100 volts in implanted pacing leads. Therefore, a shield attenuation of 1,000,000 or 60 dB is required, which requires that the maximum aperture dimension must equal 1/2000 of the wavelength. At 64 MHz, L=0.5 meters/2000=0.00025 meters or 0.25 millimeters. Since N may range from 10 to 1000, the maximum aperture dimension is further reduced to approximately 0.1 millimeters to 0.01 millimeters.

Therefore, depending upon the specific application and shield design, a maximum aperture dimension of 0.01 millimeters to 10 millimeters should be used.

Figure 32:
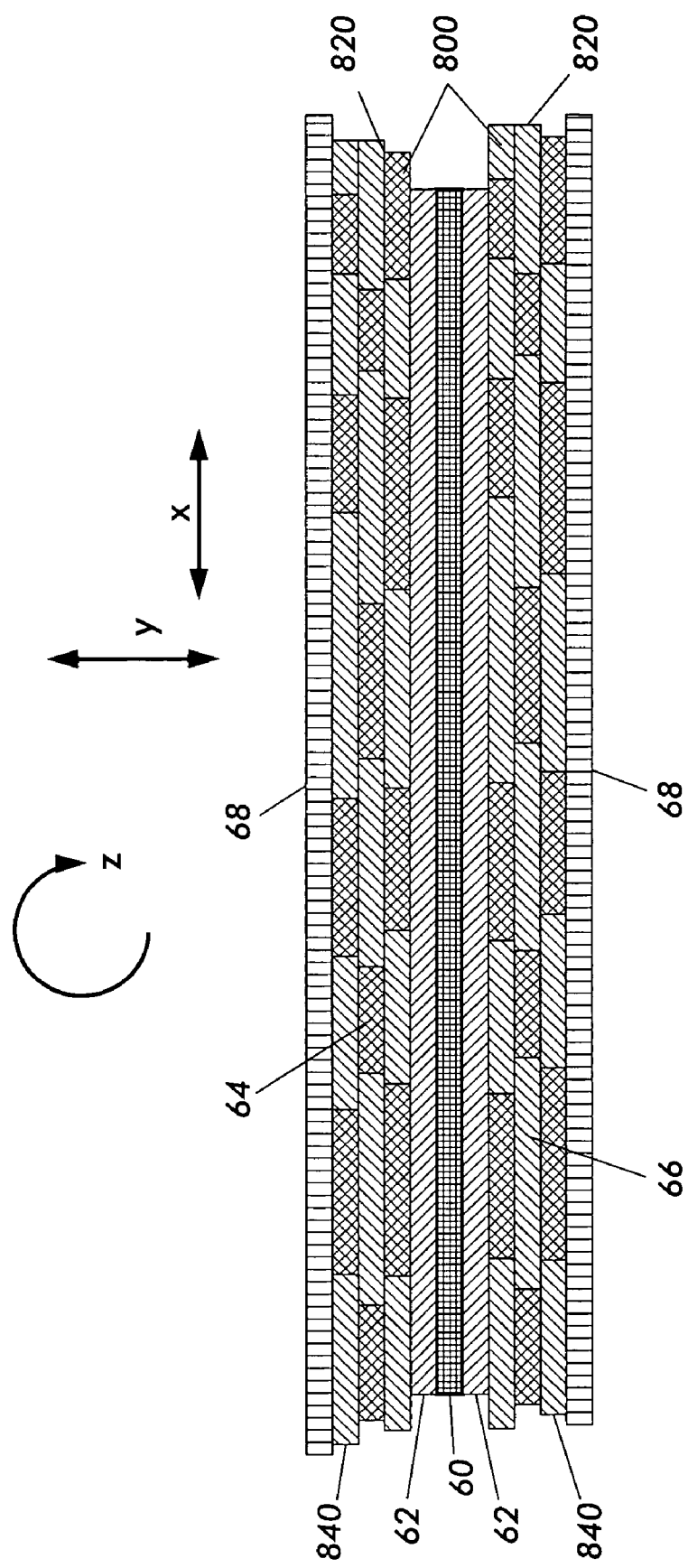
FIG. 32 is a cross-sectional view of one embodiment of an apertured shielding of a wire lead according to the concepts of the present invention.

An example of such an apertured shielding for use with an electrical lead is illustrated in FIG. 32. As shown in FIG. 32, an electrical lead 60 is initially coated with an insulation layer 62 so as to electrically insulate the electrical lead from its surroundings. Upon the insulation layer 62, a first patterned or apertured layer 800 of shielding is placed or formed thereon. The first patterned or apertured layer 800 includes conductive material 64 and non-conductive materials 66.

Upon the first patterned or apertured layer 800 of shielding, a second patterned or apertured layer 820 of shielding is placed or formed thereon. The second patterned or apertured layer 820 includes conductive material 64 and non-conductive materials 66.

It is noted that the conductive material 64 may be formed of a single integral piece of conductive material or be formed from a multitude of pieces of conductive material, the multitude of pieces being electrically connected together in such a manner to function as a single integral piece of conductive material.

Upon the second patterned or apertured layer 820 of shielding, a third patterned or apertured layer 840 of shielding is placed or formed thereon. The third patterned or apertured layer 840 includes conductive material 64 and non-conductive materials 66.

The conductive materials 64 of this embodiment of the present invention may be a metal, a carbon composite, nanotubes (wherein the nanotubes may be constructed from a carbon base or the nanotubes could be formed from other amalgams coated with the appropriate material(s)), metal-coated carbon filaments (wherein the metal may be one of the following metals: nickel, copper, cobalt, silver, gold, tin, or zinc), metal-coated ceramic filaments (wherein the metal may be one of the following metals: nickel, copper, cobalt, silver, gold, tin, or zinc), a composite of metal-coated carbon filaments and a polymer (wherein the polymer may be one of the following: polyether sulfone, silicone, polymide, polyvinylidene fluoride, or epoxy), a composite of metal-coated ceramic filaments and a polymer (wherein the polymer may be one of the following: polyether sulfone, silicone, polymide, polyvinylidene fluoride, or epoxy), a composite of metal-coated carbon filaments and a ceramic (wherein the ceramic may be one of the following: cement, silicates, phosphates, silicon carbide, silicon nitride, aluminum nitride, or titanium diboride), a composite of metal-coated ceramic filaments and a ceramic (wherein the ceramic may be one of the following: cement, silicates, phosphates, silicon carbide, silicon nitride, aluminum nitride, or titanium diboride), or a composite of metal-coated (carbon or ceramic) filaments (wherein the metal may be one of the following metals: nickel, copper, cobalt, silver, gold, tin, or zinc) and a polymer/ceramic combination (wherein the polymer may be one of the following: polyether sulfone, silicone, polymide, polyvinylidene fluoride, or epoxy and the ceramic may be one of the following: cement, silicates, phosphates, silicon carbide, silicon nitride, aluminum nitride, or titanium diboride).

A more detailed description of the coated filaments is found in U.S. Pat. No. 5,827,997, entitled "Metal Filaments for Electromagnetic Interference Shielding." The entire content of U.S. Pat. No. 5,827,997 is hereby incorporated by reference.

The non-conductive materials 66 of this embodiment of the present invention may be a ceramic; glass; mica; anodized copper; metallic oxides; natural or synthetic rubbers; or resins, such as natural resins, epoxy resins, or silicones.

Over the shielding, a biocompatible layer 68 may be placed or formed thereon. Preferably, the biocompatible layer is a non-permeable diffusion resistant biocompatible material.

As illustrated in FIG. 32, the conductive material 64 is patterned or apertured in an x-direction through the utilization of non-conductive materials 66, wherein the x-direction is a direction substantially parallel to an axis of the lead 60. In other words, the conductive material 64 is broken up, patterned, or apertured in this direction such that one non-conductive material 66 is physically separated from a neighboring non-conductive material 66 in the same layer.

Moreover, as illustrated in FIG. 32, the conductive materials 64 of different layers are patterned in a y-direction, wherein the y-direction is a direction substantially perpendicular to an axis of the lead 60. In other words, the conductive materials 64 of different layers are broken up in this direction such that one conductive material 64 is electrically isolated from a neighboring conductive material 64 in an immediate adjacent layer; i.e., a conductive material 64 in the first patterned or apertured layer 800 is electrically isolated from a neighboring conductive material 64 in the second patterned or apertured layer 82.

Preferably, the distance of the overlap is much smaller than the wavelength of the electromagnetic pulse that the shield must attenuate to prevent the incident pulse from passing unattenuated through the shield.

If the length of the overlapping shield dimension is designed to exceed the thickness of the shield material, the structure thus formed resembles a waveguide and frequencies well below its cut-off frequency are subject to additional attenuation. For a frequency of 64-128 MHz, this overlap corresponds to approximately 2-3× the maximum aperture dimension.

Therefore, depending upon the specific application and shield design, a minimum shield overlap dimension should be 2-3× the maximum aperture dimension. It is also important to note that the heating may also increase with increased frequency. At a static magnetic field of 1.5 Tesla the RF transmission frequency is 63.7 MHz, at 3 T it is 127.5 MHz (factor of 42.5 MHz for each Tesla).

Lastly, the conductive material 64 may be segmented or apertured in a z-direction, wherein the z-direction represents the planar surface of a layer as it is wrapped around the lead 60.

Figure 33:
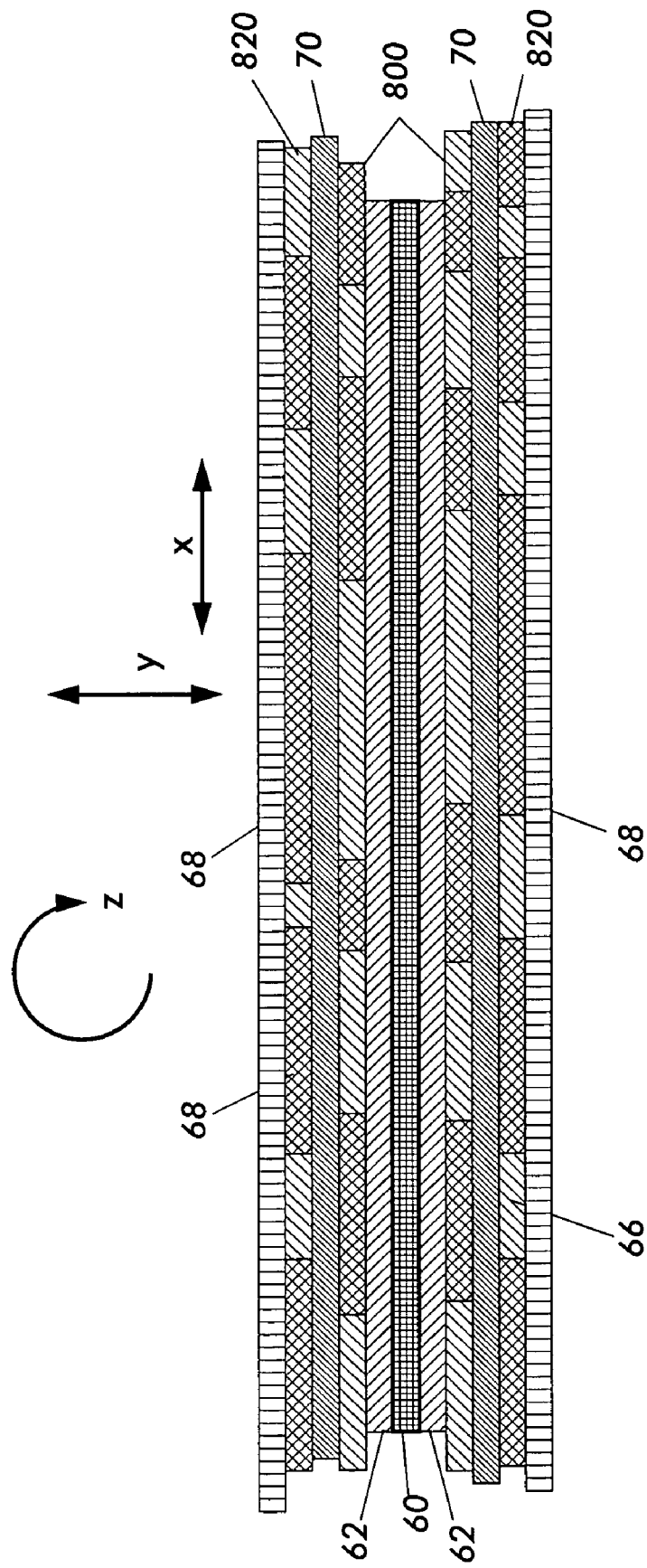
FIG. 33 is a cross-sectional view of another embodiment of an apertured shielding of a wire lead according to the concepts of the present invention.

Another example of such a shielding for use with an electrical lead is illustrated in FIG. 33. As shown in FIG. 33, an electrical lead 60 is initially coated with an insulation layer 62 so as to electrically insulate the electrical lead from its surroundings. Upon the insulation layer 62, a first patterned or apertured layer 800 of shielding is placed or formed thereon. The first patterned or apertured layer 800 includes conductive material 64 and non-conductive materials 66.

It is noted that the conductive material 64 may be formed of a single integral piece of conductive material or be formed from a multitude of pieces of conductive material, the multitude of pieces being electrically connected together in such a manner to function as a single integral piece of conductive material.

Upon the first patterned or apertured layer 800 of shielding, a layer.70 of non-conductive material is placed or formed thereon. Upon the layer 70 of non-conductive material, a second patterned or apertured layer 820 of shielding is placed or formed thereon. The second patterned or apertured layer 820 includes conductive material 64 and non-conductive materials 66.

The conductive materials 64 of this embodiment of the present invention may be a metal, a carbon composite, nanotubes (wherein the nanotubes may be constructed from a carbon base or the nanotubes could be formed from other amalgams coated with the appropriate material(s)), metal-coated carbon filaments (wherein the metal may be one of the following metals: nickel, copper, cobalt, silver, gold, tin, or zinc), metal-coated ceramic filaments (wherein the metal may be one of the following metals: nickel, copper, cobalt, silver, gold, tin, or zinc), a composite of metal-coated carbon filaments and a polymer (wherein the polymer may be one of the following: polyether sulfone, silicone, polymide, polyvinylidene fluoride, or epoxy), a composite of metal-coated ceramic filaments and a polymer (wherein the polymer may be one of the following: polyether sulfone, silicone, polymide, polyvinylidene fluoride, or epoxy), a composite of metal-coated carbon filaments and a ceramic (wherein the ceramic may be one of the following: cement, silicates, phosphates, silicon carbide, silicon nitride, aluminum nitride, or titanium diboride), a composite of metal-coated ceramic filaments and a ceramic (wherein the ceramic may be one of the following: cement, silicates, phosphates, silicon carbide, silicon nitride, aluminum nitride, or titanium diboride), or a composite of metal-coated (carbon or ceramic) filaments (wherein the metal may be one of the following metals: nickel, copper, cobalt, silver, gold, tin, or zinc) and a polymer/ceramic combination (wherein the polymer may be one of the following: polyether sulfone, silicone, polymide, polyvinylidene fluoride, or epoxy and the ceramic may be one of the following: cement, silicates, phosphates, silicon carbide, silicon nitride, aluminum nitride, or titanium diboride).

Over the shielding, a biocompatible layer 68 may be placed or formed thereon. Preferably, the biocompatible layer is a non-permeable diffusion resistant biocompatible material.

The non-conductive materials 66 of this embodiment of the present invention may be a ceramic; glass; mica; anodized copper; metallic oxides; natural or synthetic rubbers; or resins, such as natural resins, epoxy resins, or silicones.

As illustrated in FIG. 4, the conductive materials 64 are patterned or apertured in an x-direction, wherein the x-direction is a direction substantially parallel to an axis of the lead 60. In other words, the conductive materials 64 are broken up, patterned, or apertured in this direction such that the non-conductive materials 66 break up the conductive material 64.

Moreover, as illustrated in FIG. 33, the conductive materials 64 are patterned in a y-direction, wherein the y-direction is a direction substantially perpendicular to an axis of the lead 60. In other words, the conductive materials 64 are broken up in this direction such that one conductive material 64 is electrically isolated from a neighboring conductive material 64 in an immediate adjacent layer; i.e., a conductive material 64 in the first patterned or apertured layer 800 is electrically isolated from a neighboring conductive material 64 in the second patterned or apertured layer 820.

Preferably, the distance of the overlap is much smaller than the wavelength of the electromagnetic pulse that the shield must attenuate to prevent the incident pulse from passing unattenuated through the shield.

If the length of the overlapping shield dimension is designed to exceed the thickness of the shield material, the structure thus formed resembles a waveguide and frequencies well below its cut-off frequency are subject to additional attenuation. For a frequency of 64-128 MHz, this overlap corresponds to approximately 2-3× the maximum aperture dimension.

Therefore, depending upon the specific application and shield design, a minimum shield overlap dimension should be 2-3× the maximum aperture dimension.

Lastly, the conductive materials 64 may be segmented in a z-direction, wherein the z-direction represents the planar surface of a layer as it is wrapped around the lead 60.

As noted above, the conductive material 64 is patterned or apertured to limit the build up of eddy currents. Examples of the patterning or aperturing of the conductive material 64 are illustrated in FIGS. 34-36.

Figure 34:
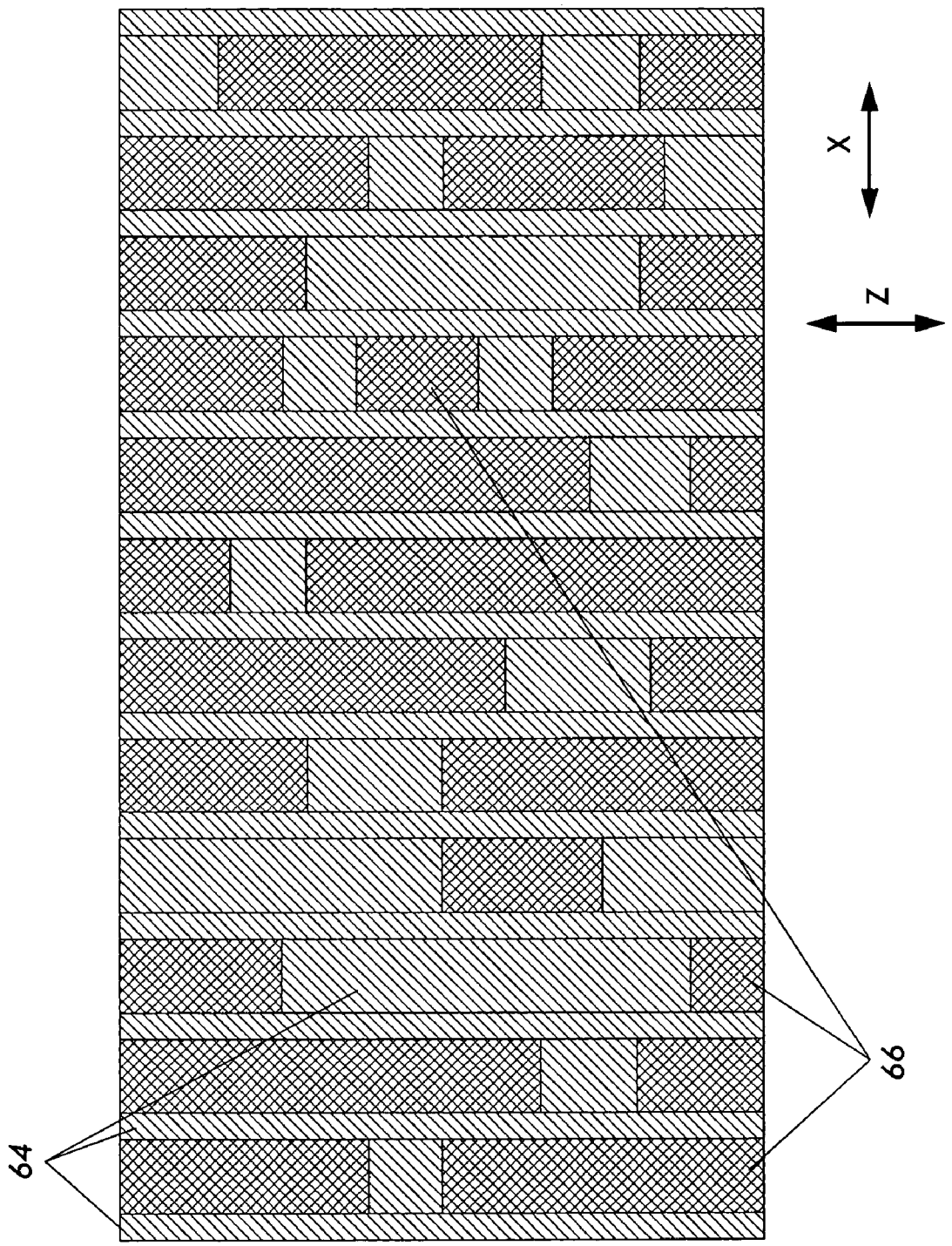
FIG. 34 is a top view of a layer of an embodiment of the apertured shielding, having a predetermined apertured pattern of non-conductive materials, for a wire lead shielding according to the concepts of the present invention.

FIG. 34 illustrated a top view of a fabricated layer of the shielding. As illustrated in FIG. 34, the conductive material 64 is patterned or apertured in such a way that a width of the conductive material 64 in the x-direction, the x-direction being substantially parallel to an axis of a lead, is substantially equal. More specifically, the conductive material 64 is patterned or apertured in such a way that non-conductive materials 66 spaced in a predetermined manner; e.g., the spacing between the non-conductive materials 66, in the x-direction, may be equal or set in a predetermined manner. Lastly, the spacing between non-conductive materials 66 in a z-direction, the z-direction representing the planar surface of a layer as it is wrapped around a lead, is not necessarily equal or set in a predetermined manner; however the spacing in the z-direction may be equal or set in a predetermined manner.

Preferably, the distance of the overlap is much smaller than the wavelength of the electromagnetic pulse that the shield must attenuate to prevent the incident pulse from passing unattenuated through the shield.

If the length of the overlapping shield dimension is designed to exceed the thickness of the shield material, the structure thus formed resembles a waveguide and frequencies well below its cut-off frequency are subject to additional attenuation. For a frequency of 64-128 MHz, this overlap corresponds to approximately 2-3× the maximum aperture dimension.

Therefore, depending upon the specific application and shield design, a minimum shield overlap dimension should be 2-3× the maximum aperture dimension.

FIG. 35 illustrated a top view of a fabricated layer of the shielding. As illustrated in FIG. 35, the conductive material 64 is patterned or apertured in such a way that a width of the conductive material 64 in the z-direction, the z-direction representing the planar surface of a layer as it is wrapped around a lead, is substantially equal. More specifically, the conductive material 64 is patterned or apertured in such a way that non-conductive materials 66 spaced in a predetermined manner; e.g., the spacing between the non-conductive materials 66, in the z-direction, may be equal or set in a predetermined manner. Lastly, the spacing between non-conductive materials 66 in a x-direction, the x-direction being substantially parallel to an axis of a lead, is not necessarily equal or set in a predetermined manner; however the spacing in the x-direction may be equal or set in a predetermined manner.

Preferably, the distance of the overlap is much smaller than the wavelength of the electromagnetic pulse that the shield must attenuate to prevent the incident pulse from passing unattenuated through the shield.

If the length of the overlapping shield dimension is designed to exceed the thickness of the shield material, the structure thus formed resembles a waveguide and frequencies well below its cut-off frequency are subject to additional attenuation. For a frequency of 64-128 MHz, this overlap corresponds to approximately 2-3× the maximum aperture dimension.

Therefore, depending upon the specific application and shield design, a minimum shield overlap dimension should be 2-3× the maximum aperture dimension.

FIG. 36 illustrated a top view of a fabricated layer of the shielding. As illustrated in FIG. 36, the conductive material 64 is patterned or apertured in such a way that the widths of the non-conductive materials 66 in the z-direction, the z-direction representing the planar surface of a layer as it is wrapped around a lead, are random. More specifically, the conductive materials 64 are patterned or apertured in such a way that non-conductive materials 66 spaced in a random manner. Lastly, the spacing between non-conductive materials 66 in an x-direction, the x-direction being substantially parallel to an axis of a lead, is also random.

It is noted that the although FIGS. 32-36 show a patterned or apertured shielding with respect to a lead, the patterned or apertured shielding can be used to shield other shaped devices such as electrical component housings or other components of a medical assist device/system.

It is further noted that the actual dimensions of the non-conductive materials can be set to suppress the radiation and eddy currents induced from specific frequencies; e.g., the lengths of the non-conductive material can be varied to suppress or block specific or undesired radiation frequencies. The dimensions of the non-conductive material would be on the order of the wavelength of the radiation so as to suppress, block, or shield the radiation.

Preferably, the distance of the overlap is much smaller than the wavelength of the electromagnetic pulse that the shield must attenuate to prevent the incident pulse from passing unattenuated through the shield.

The actual layers may be formed using a photoresist/masking process such as used in integrated circuit fabrication and thin film deposition. By using a mask/photoresist process, the conductive/insulative layers in the vertical direction can be easily formed so that the conductive/insulative layers alternate (radially outward from the axis of the lead), and the conductive/insulative layers in the horizontal direction also alternate (substantially parallel to an axis of the lead).

Although, as stated above, eddy currents in a conductive structure may cause heating to the surrounding tissue, eddy currents induced in the tissue may also cause the heating of the surrounding tissue. As noted above, when a substance such as human tissue is subjected to a static magnetic field, the individual magnetic moments of the spins in the tissue align in a parallel and anti-parallel direction with the static magnetic field. This direction along the static magnetic field can be termed as the longitudinal direction. In magnetic-resonance imaging, the radio frequency polarizing field used for spin manipulation is constantly changing and thus, the individual magnetic moments of the spins in the tissue attempt to align with the polarizing field. The constant changing of alignment of the magnetic moments of the spins in the tissue causes the tissue's temperature to increase, thereby exposing the tissue to possible magnetic-resonance imaging induced thermal damage. Thus, this second possible cause of undesirable heat needs to also be addressed to prevent tissue damage caused by excessive heat.

In a further embodiment of the present invention, the heat being accumulated in the surrounding tissue is addressed and reduced or prevented, notwithstanding the source or cause of the excessive heat. To better describe this embodiment, the term, specific absorption ratio, will be used in discussing the excessive heat.

The specific absorption ratio is defined as the amount of power absorbed by a sample within a magnetic-resonance imaging scanner. The sample could be a suitable phantom mimicking tissue properties or a tissue region of patient.

As noted above, this excessive heat could be caused by either eddy currents induced in conductive structures or eddy currents induced in the actual tissue. It is noted that although two distinct sources of excessive heat are identified for the purposes of describing this embodiment of the present invention, the actual source of the heat may not be known, nor is it a real consideration in the actual functionality of this embodiment of the present invention.

With respect to induced eddy currents, due to their electromagnetic receptive capabilities, cardiac assist device leads, metallic guidewires, neurostimulator leads and intraluminal coil leads may induce a localized increase in the specific absorption ratio, thereby resulting in an increased heating of the surrounding tissue. Moreover, due to the individual magnetic moments of the spins in the tissue attempting to align with the polarizing field, the acquisition sequence of the magnetic-resonance imaging process may also induce a localized increase in the specific absorption ratio, thereby resulting in an increased heating of the surrounding tissue. This tissue heating, notwithstanding the source, may be a function of the time of radio-frequency excitation, gradient coil switching speed, or strength of the static magnetic field.

In this embodiment of the present invention, the localized specific absorption ratio of tissue is reduced by altering the actual magnetic-resonance imaging acquisition process. More specifically, according to a preferred embodiment of the present invention, the localized specific absorption ratio of tissue is reduced by varying the imaging pulse sequence and/or changing the timing parameters of magnetic-resonance imaging acquisition process. For example, in response to increases in the localized specific absorption ratio or during magnetic-resonance image acquisition, the radio-frequency excitation cycle may be interrupted to allow for cooling of the tissue. In other words, if a threshold temperature level or a localized specific absorption ratio is exceeded, the magnetic-resonance imaging acquisition can be halted until the tissue temperature or localized specific absorption ratio decreases to an accepted level.

It is noted that the increased in the localized specific absorption ratio may or may not have resulted from placement of a conductive structure near the tissue region.

Figure 8:
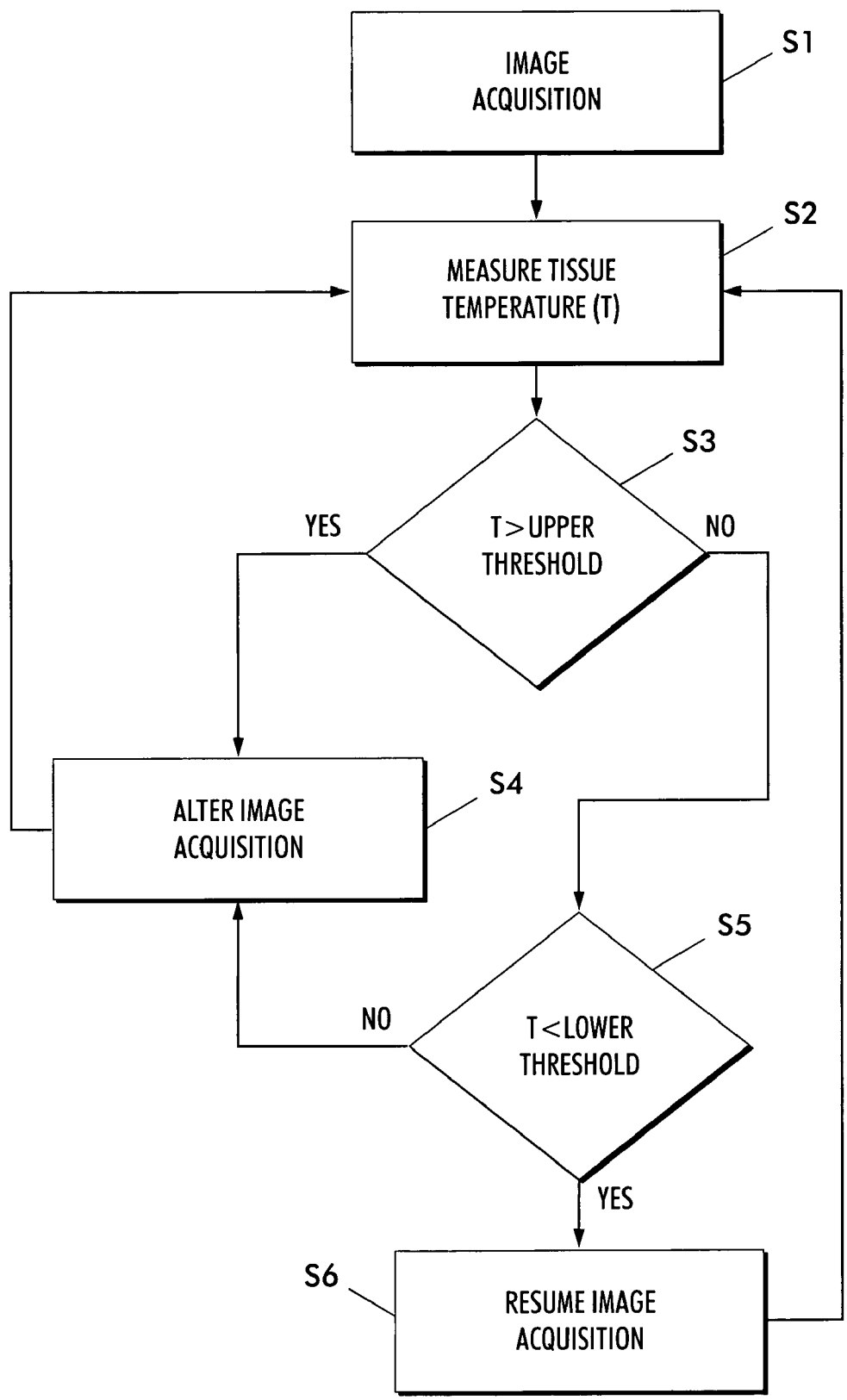
FIG. 8 is a flowchart illustrating the altering of a magnetic-resonance imaging acquisition process in response to a measured temperature of the tissue region being imaged, according to the concepts of the present invention.

FIG. 8 illustrates a magnetic-resonance imaging process according to the concepts of the present invention, which alters the actual magnetic-resonance imaging acquisition process in response to a temperature change in the tissue region being imaged. In this process, at Step S1, an image acquisition sequence is started by the magnetic-resonance imaging system. At step S2, the temperature change in the tissue region being imaged is measured. It is noted that this temperature change may be relative or absolute. The temperature change in the tissue region being imaged can be measured a number of ways.

For example, in one embodiment, the relative temperature change can be monitored by magnetic image acquisition techniques. More specifically, relative temperature changes can be measured using a double gradient echo sequence to acquire a baseline phase image and a second phase image at within a single radio-frequency excitation of one same pulse sequence. A relative spatial temperature map of the desired region of interest can be calculated based on the subtraction of the two phase images collected during the double gradient echo sequence acquisition.

A more detail description of this relative temperature change acquisition process is described in U.S. Pat. No. 5,711,300, entitled "Real Time In Vivo Measurement Of Temperature Changes With Magnetic-resonance Imaging." The entire contents of U.S. Pat. No. 5,711,300 are hereby incorporated by reference. It is noted that this is only one example of collecting phase image data for relative temperature mapping. Other methods for collecting phase image data for relative temperature mapping may also be used.

It is further noted that absolute temperature changes can be determined using known methods, such as fiber optic thermocouples attached to guidewires or catheters, or non-contact thermographic imaging techniques.

Upon calculating the temperature change of the desired tissue region, such as described above with respect to the relative spatial temperature map of the desired region of interest, at Step S3, a predetermined upper temperature threshold is compared with the calculated temperature change, or in the example described above, compared with the relative temperature map. If the temperature change exceeds or is equal to the predetermined upper temperature threshold, the imaging acquisition sequence is adjusted or halted so as to reduce the temperature change below the predetermined upper temperature threshold, at Step S4.

The process returns to Step S2 to make another determination of the temperature change in the tissue region of interest. If the temperature change is below the predetermined upper temperature threshold, Step S5 determines if the measured temperature change is above a predetermined lower temperature threshold. If Step S5 determines that the measured temperature change is above a predetermined lower temperature threshold, the process returns to Step S4 and the imaging acquisition sequence remains adjusted or halted so as to reduce the temperature of the tissue region of interest. On the other hand, if Step S5 determines that the measured temperature change is below or is equal to a predetermined lower temperature threshold, the process resume image acquisition at to Step S6.

It is to be understood that this type of adjustment can be applied to any form of pulse sequence or imaging acquisition method so as it meets the requirements of the user. There are an infinite number of variations in pulse sequence design and pulse sequence parameter determination to minimize heating. The actual variation in pulse sequence design and pulse sequence parameter determination will be dependent upon the image quality and the temporal resolution of acquisition desired, however, the required tissue temperature threshold (s) will be the ultimate determinant.

This embodiment may also include a user interactive process, which can be programmed. An example of such a process is described in detail in U.S. Pat. No. 6,396,266, entitled "magnetic-resonance Imaging System With Interactive magnetic-resonance Geometry Prescription Control." The entire contents of U.S. Pat. No. 6,396,266 are hereby incorporated by reference.

In another embodiment, the SAR coefficients of a wide range of implantable medical devices are programmed into the magnetic-resonance imaging system, which then uses these data to predetermine and apply as safe magnetic-resonance imaging sequence.

Figure 9:
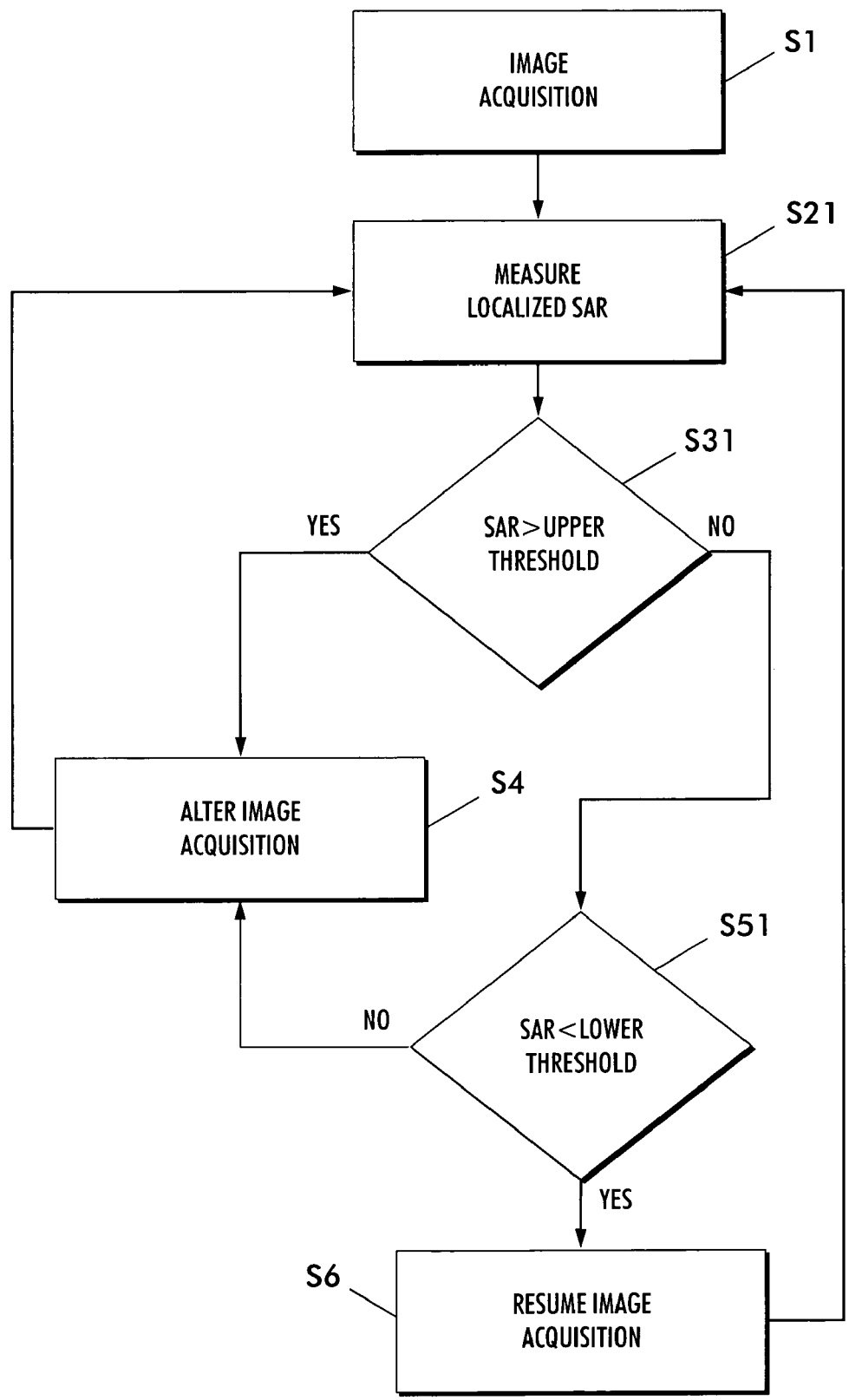
FIG. 9 is a flowchart illustrating the altering of a magnetic-resonance imaging acquisition process in response to a measured localized specific absorption ratio of the tissue region being imaged, according to the concepts of the present invention.

In yet another embodiment, as illustrated in FIG. 9, a magnetic-resonance imaging process, according to the concepts of the present invention, alters the actual magnetic-resonance imaging acquisition process in response to a calculated specific absorption ratio of the tissue region being imaged. In this process, at Step S1, an image acquisition sequence is started by the magnetic-resonance imaging system. At step S21, the specific absorption ratio is estimated using theoretical modeling and/or empirical results from certain conductors being imaged in tissues. At Step S31, the calculated specific absorption ratio level(s) are then be compared to threshold levels.

If the calculated specific absorption ratio level exceeds or is equal to the predetermined upper specific absorption ratio level threshold, the imaging acquisition sequence is adjusted or halted so as to reduce the temperature of the tissue region of interest, at Step S4.

The process returns to Step S21 to make another determination of the specific absorption ratio level. If the determined specific absorption ratio level is below the predetermined upper specific absorption ratio level threshold, Step S51 determines if the determined specific absorption ratio level is above a predetermined lower specific absorption ratio threshold. If Step S51 determines that the determined specific absorption ratio level is above a predetermined lower specific absorption ratio threshold, the process returns to Step S4 and the imaging acquisition sequence remains adjusted or halted so as to reduce the temperature of the tissue region of interest. On the other hand, if Step S51 determines that the determined specific absorption ratio level is below or is equal to a predetermined lower specific absorption ratio threshold, the process resume image acquisition at to Step S6.

This embodiment may also include a user interactive process described above.

In the embodiments illustrated in FIGS. 8 and 9, specific absorption ratio or energy deposition of radio frequency energy in the tissue can be reduced by specific manipulations of each individual radio frequency pulse. Moreover, these embodiments of the present invention may manipulate the pulse waveform, pulse duration and pulse amplitude to reduce the specific absorption ratio. The choice of the integrated values of these three parameters is determined upon by the requirements of the user. For example, reduction of the amplitude and increase in the duration of the pulse may reduce the specific absorption ratio, but this may not be appropriate for the specified timing required to image certain contrast parameters.

A more detail discussion of the specific manipulations that be used to reduce specific absorption ratio is set forth in U.S. Pat. No. 4,760,336, entitled "Variable Rate Magnetic Resonance Selective Excitation For Reducing radio-frequency Power And Specific Absorption Rate." The entire contents of U.S. Pat. No. 4,760,336 are hereby incorporated by reference.

It is also noted that the embodiments illustrated in FIGS. 8 and 9 can be used not only as a stand-alone solution to reduce the increases in specific absorption ratio resulting from conductive structures in tissue, but also in conjunction with the patterned shielding embodiments described above.

Figure 10:
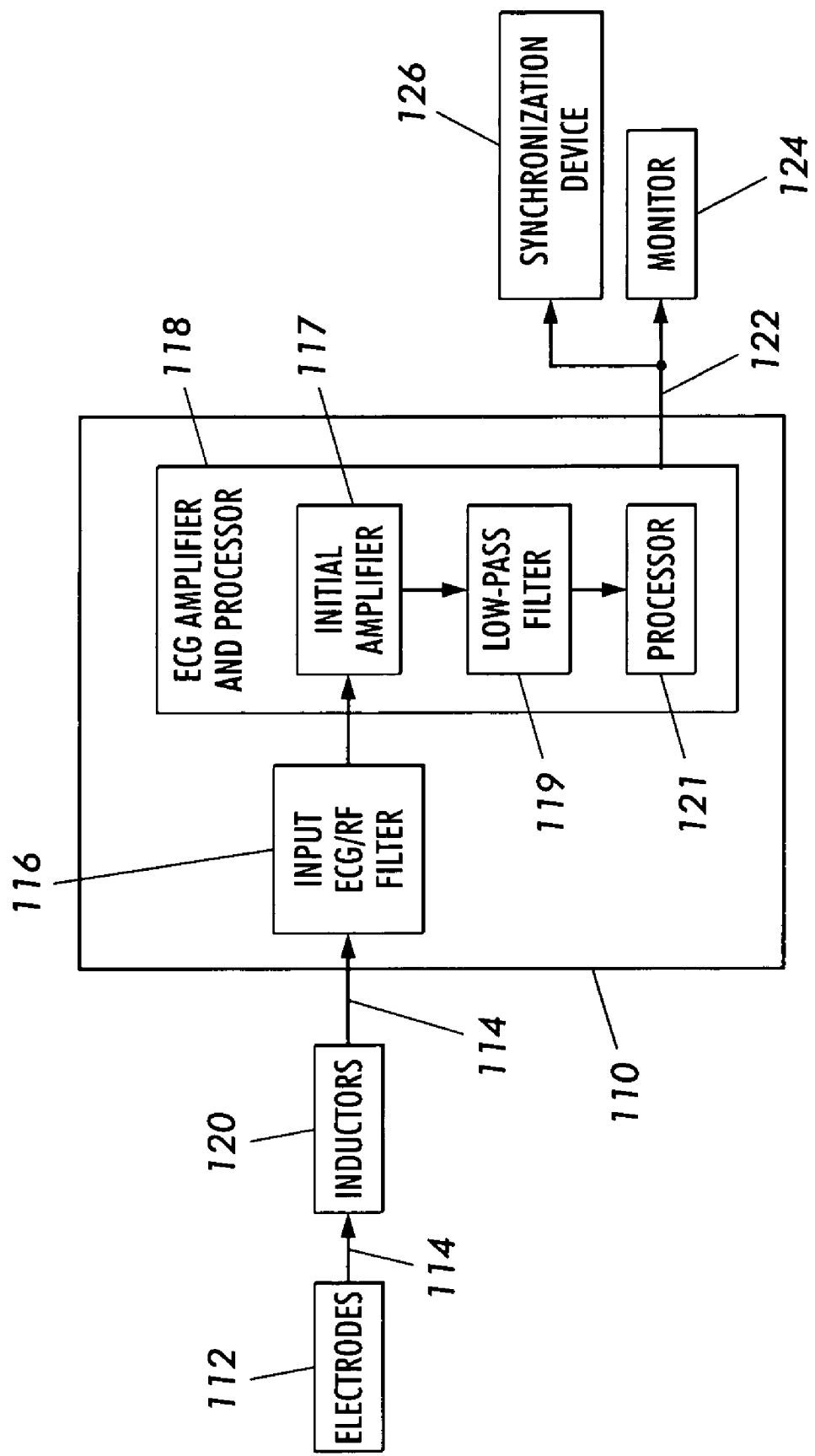
FIG. 10 is a block diagram of an ECG amplifier capable of operating in the high static magnetic field, radio-frequency field, and gradient field environment produced in a magnetic-resonance imaging system, according to the concepts of the present invention.

A block diagram of an ECG acquisition and processing system is shown in FIG. 10. The ECG monitoring system can be used as a stand-alone ECG monitor or as part of an external or internal pacemaker. A patient is connected to ECG monitoring circuitry 110 via surface or internal electrodes 112 and lead wires 114. The lead wires 114 connect to the input ECG/radio-frequency filter 116.

This filter design enables the monitoring circuit to operate in the high radio-frequency field environment generated by the magnetic-resonance imaging system. First, the radio-frequency filter prevents the development of excess voltage on the ECG input amplifier and processor 118 that would otherwise damage the amplifier, and excess voltage on the ECG leads potentially inducing a dangerous heart rhythm. Second, it prevents the development of excess current on the ECG electrodes 112 that would induce thermogenic damage at the electrode-heart tissue interface that could lead to loss of capture of pacing signals and possibly death. Third, the radio-frequency filter 116, when attached between the lead wires 114 and the ECG input amplifier, will not interfere with proper sensing of the ECG signal.

The input ECG/radio-frequency filter 116 has the characteristics of a low-pass filter with approximately 100 dB signal attenuation in the commonly used magnetic-resonance imaging system radio-frequency frequency range. The frequencies contained in the intracardiac or surface ECG signal, however, are passed without any attenuation.

In the case where the lead wires 114 are of long length, such as in external monitoring, there is significant stray capacitance between the lead wires. As a result, electromagnetic fields generated between the electrodes 112 can produce dangerously high voltage within and current flow through the electrodes.

To limit this voltage and current, inductors 120, may be placed in the lead wires 114, close to the electrodes. The ECG/radio-frequency input filter 116 and lead wire inductors 120 must contain components with a resonance frequency higher than the radio-frequency frequency of the magnetic-resonance imaging system in use.

The ECG amplifier/processor 118 contains low-pass or band reject filter 119 placed after the initial amplifier 117 and before final stages 121. The low-pass or band reject filter must pass the QRS signals and reject gradient field and radio-frequency frequencies. The output ECG signal 122, which can take any conventional form such as an R-wave detector output or analog ECG, can be used for any purpose. It can be used to display the ECG on monitor 124, or synchronize an external or internal device 126, such as a magnetic-resonance imaging system or cardiac pacemaker.

Figure 11:
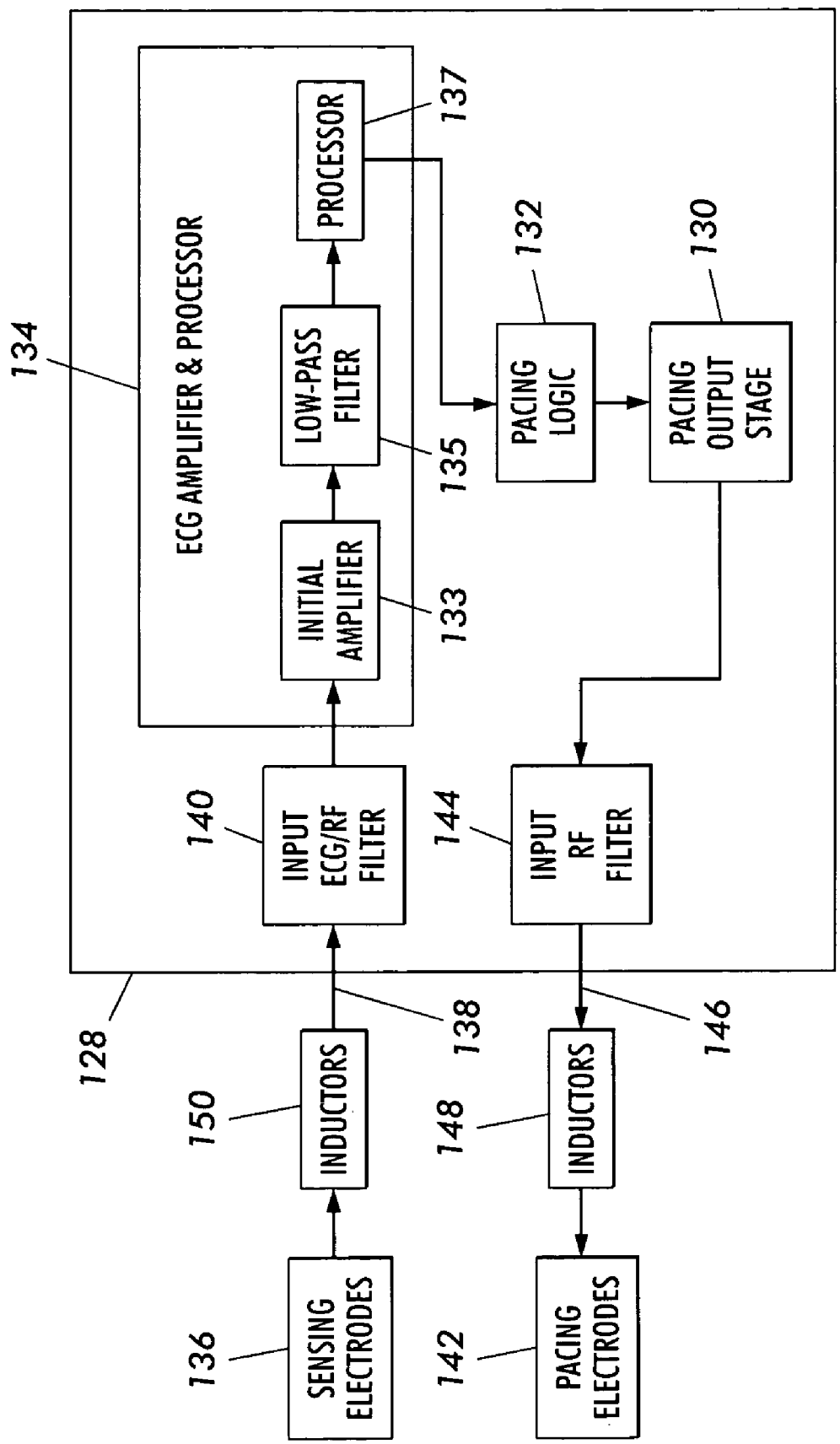
FIG. 11 is a block diagram of a pacemaker capable of operating in the high static magnetic fields, radio-frequency field, and gradient field environment produced in a magnetic-resonance imaging system, according to the concepts of the present invention.

In another embodiment shown in FIG. 11, a pacemaker system 128 is described. This pacemaker system can be either external or implantable. In addition to the elements shown in FIG. 10, this embodiment also contains a pacing output stage 130 that is controlled by the pacing logic 132.

The pacing logic is itself controlled by signals from the ECG amplifier/processor 134. The patient is connected to the pacemaker system 128, via surface or internal sensing electrodes 136 and lead wires 138. The lead wires are connected to the ECG amplifier/processor 134, via the input ECG/radio-frequency filter 140. The pacing output stage 130 is connected to pacing electrodes 142 via the output radio-frequency filter 144 and pacing lead wires 146. The ECG amplifier/processor 134 contains a low-pass or band reject filter 135 placed after the initial amplifier 133 and before the final stages 137.

The low-pass or band reject filter must pass the QRS signal and reject gradient field frequencies caused by the magnetic-resonance imaging. As in the previous embodiment, inductors 148, 150 may be placed in the lead wires, 138, 146 close to the electrodes 136, 142. In this embodiment, the sensing 136 and pacing 142 electrodes, wires 138, 146, inductors 148, 150, and radio-frequency filters 149, 144 are shown separately. However, these components can be merged to create a combined ECG sensing/pacing radio-frequency electrodes, wires, inductors, and filters.

Figure 12:
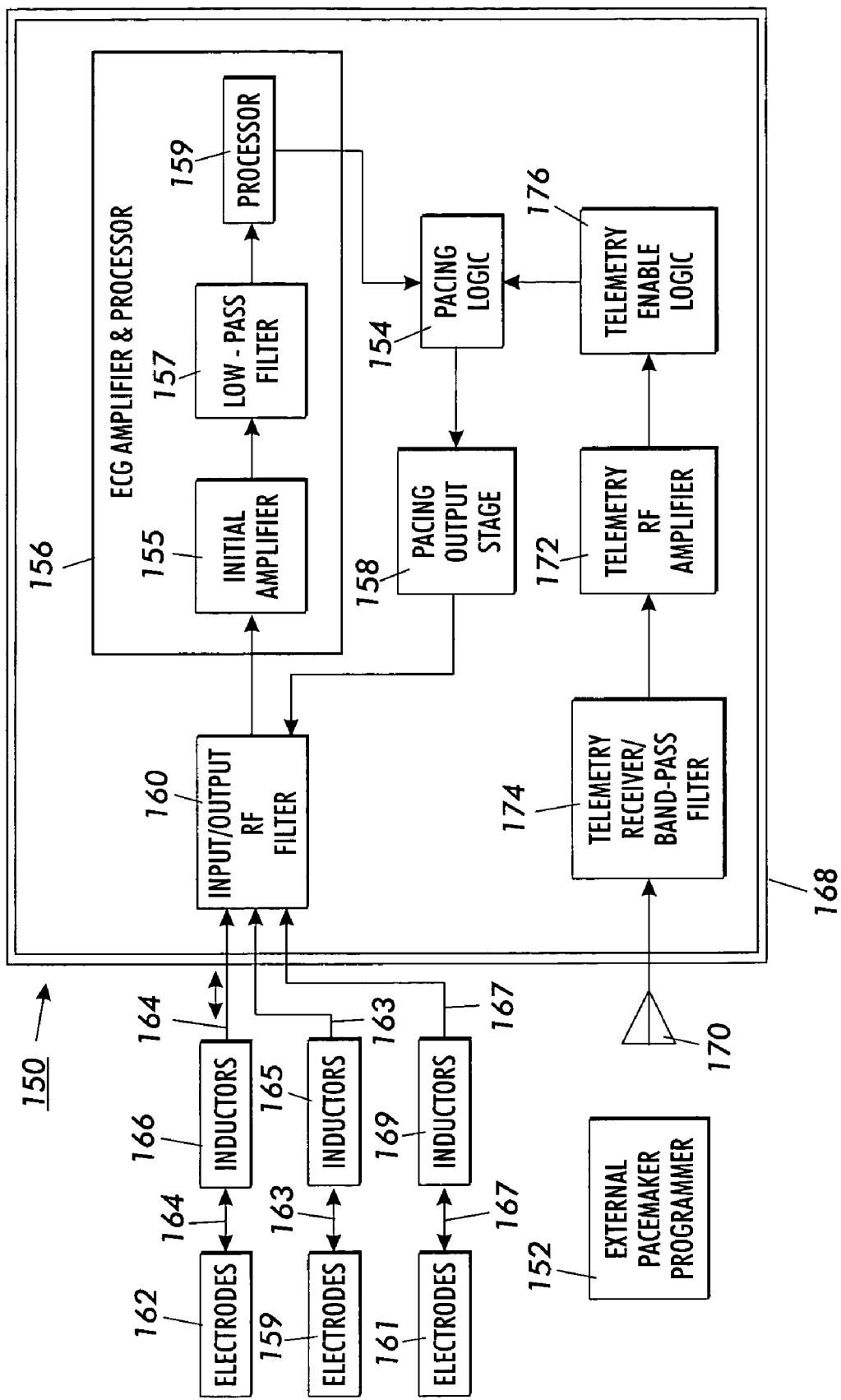
FIG. 12 is a block diagram of an implantable pacemaker, designed for external programming, which operates safely in the environment produced in a magnetic-resonance imaging system, according to the concepts of the present invention.

An implantable pacemaker 150 capable of bi-directional communication with an external programmer 152 is shown in FIG. 12. The implantable unit contains conventional programmable pacing logic 154 for sensing and/or pacing the ventricle and/or atrium and includes an ECG amplifier and processor 156, pacing output stage 158, combined input/output radio-frequency filter 160, electrodes 162 and leads 164. The ECG amplifier and processor 156 contains a low-pass or band reject filter 157 placed after the initial amplifier 155 and before final stages 159. The low-pass or band reject filter must pass the QRS signals and reject gradient field frequencies caused by the magnetic-resonance imaging.

As in the previous embodiment, inductors 166 may be placed in the lead wires 164 close to the electrodes 162. The electrodes 162, leads 164, inductors 166, and input/output filter 160 may be single elements performing combined input and output functions or may be separate input and output elements. For dual chamber pacemakers, multiple sets of sensing/pacing electrodes may be used 159, 162, which are each connected to input/output radio-frequency filters 160.

A first electrode pair may be for atrium sensing or pacing and a second electrode pair may be for ventricle sensing or pacing. As is taught in the pacing art, pacing logic 154 may be programmed, for example, to sense the atrium signal and pace via the ventricle electrodes. In addition, a new form of circulatory support called cardiomyoplasty may utilize other electrodes 161 and leads 167 to pace skeletal muscle wrapped around the heart and stimulated in synchrony with pacing the heart. In each type of pacemaker the leads 163, 164, 167 may contain inductors 165, 166, 169 to reduce electrical currents across the electrodes and each lead may be connected to separate input/output radio-frequency filter 160.

In order to protect the pacemaker from the effects of the radio-frequency field generated by the magnetic-resonance imaging system, it is necessary to surround the components with a radio-frequency shield 168. In a preferred embodiment of the present invention, this shield is as described above with respect to FIGS. 3 through 7.

More specifically, the shield may consist of patterned layers including conductive materials and non-conductive materials. The conductive materials of the present invention may be a metal, a carbon composite, nanotubes (wherein the nanotubes may be constructed from a carbon base or the nanotubes could be formed from other amalgams coated with the appropriate material(s)), metal-coated carbon filaments (wherein the metal may be one of the following metals: nickel, copper, cobalt, silver, gold, tin, or zinc), metal-coated ceramic filaments (wherein the metal may be one of the following metals: nickel, copper, cobalt, silver, gold, tin, or zinc), a composite of metal-coated carbon filaments and a polymer (wherein the polymer may be one of the following: polyether sulfone, silicone, polymide, polyvinylidene fluoride, or epoxy), a composite of metal-coated ceramic filaments and a polymer (wherein the polymer may be one of the following: polyether sulfone, silicone, polymide, polyvinylidene fluoride, or epoxy), a composite of metal-coated carbon filaments and a ceramic (wherein the ceramic may be one of the following: cement, silicates, phosphates, silicon carbide, silicon nitride, aluminum nitride, or titanium diboride), a composite of metal-coated ceramic filaments and a ceramic (wherein the ceramic may be one of the following: cement, silicates, phosphates, silicon carbide, silicon nitride, aluminum nitride, or titanium diboride), or a composite of metal-coated (carbon or ceramic) filaments (wherein the metal may be one of the following metals: nickel, copper, cobalt, silver, gold, tin, or zinc) and a polymer/ceramic combination (wherein the polymer may be one of the following: polyether sulfone, silicone, polymide, polyvinylidene fluoride, or epoxy and the ceramic may be one of the following: cement, silicates, phosphates, silicon carbide, silicon nitride, aluminum nitride, or titanium diboride).

Since the implantable pacemaker shown in FIG. 12 is enclosed in a radio-frequency shield, it was necessary to develop a unique method of external programming. The information received by the pacemaker 150 is processed to separate the desired communication signal from the radio-frequency signals produced by the magnetic-resonance imaging system. An antenna 170 is connected to the telemetry radio-frequency amplifier 172 via the telemetry receiver/band pass filter 174. This filter is a band pass filter that passes only the specific programming frequency to the telemetry amplifier 172.

The telemetry logic circuit 176 interprets all radio-frequency received by the telemetry antenna 170 and will only allow programming of the pacing logic circuit 154 when a specific telemetry enable pattern is received. The telemetry enable logic circuit 176 will also inhibit control of the pacing output stage 158 while programming is taking place. This prevents improper and potentially dangerous pacing parameters from controlling the pacing stage. As a further safety measure, the telemetry enable circuit 176 enables pacing at a preset rate ("safety pacing") to provide adequate pacing back-up for pacemaker dependent patients during external programming.

Figure 13:
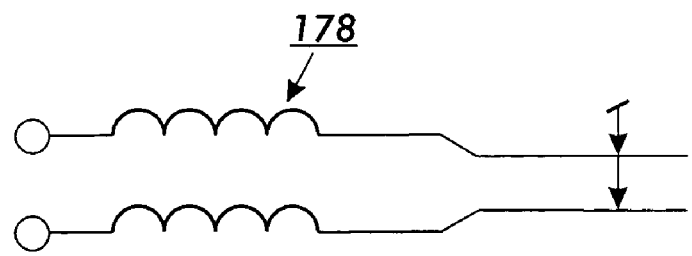
FIGS. 13 through 18 are schematic drawings of various ECG lead and/or harness configurations designed for operation in the environment produced by an magnetic-resonance imaging system, according to the concepts of the present invention.
Figure 14:
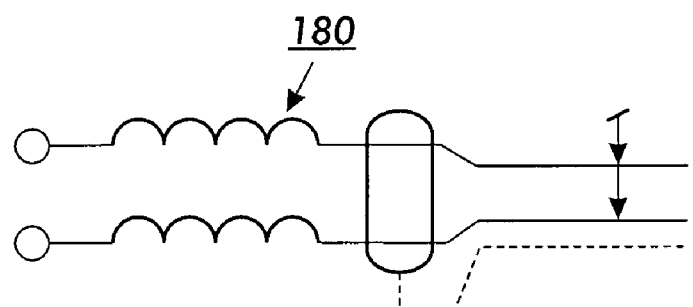
Figure 15:
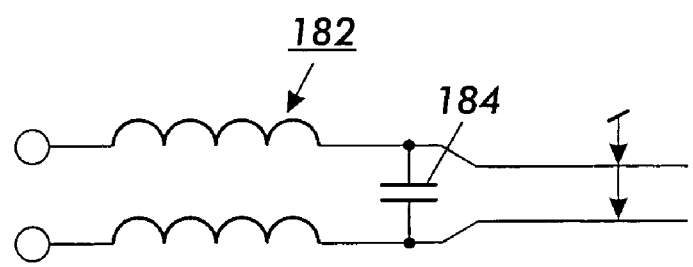
Figure 16:
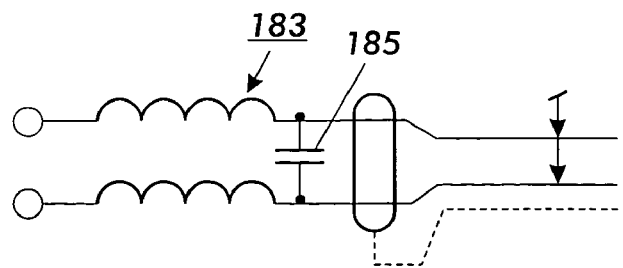
Figure 17:
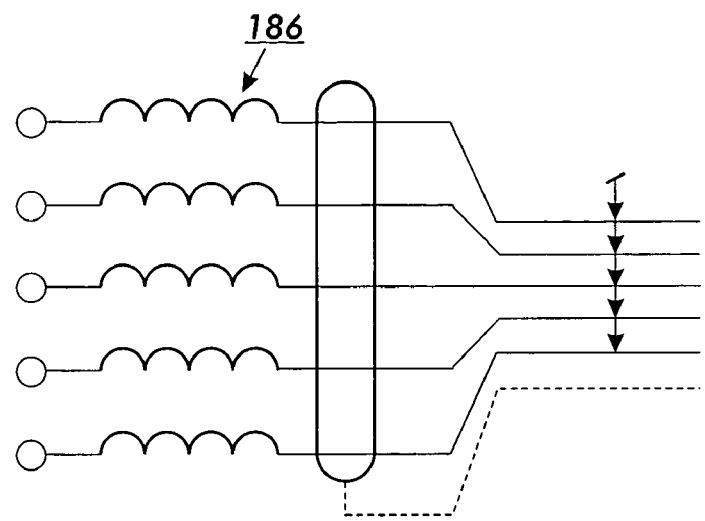
Figure 18:
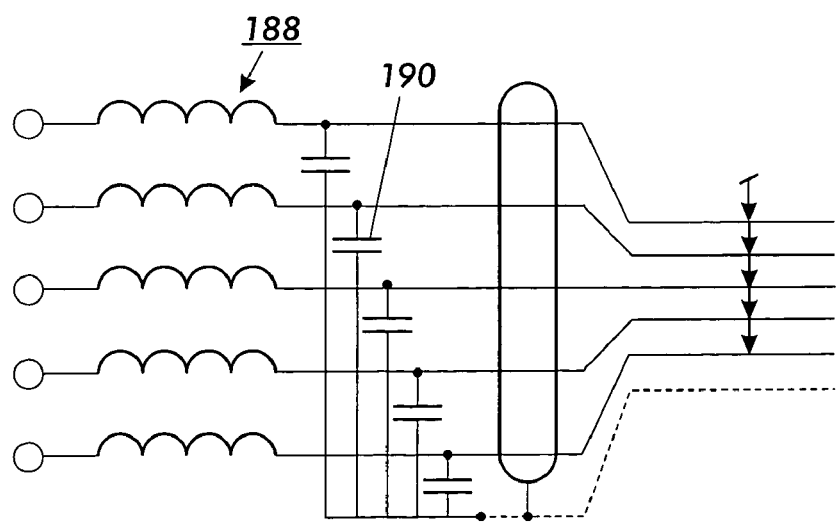

FIGS. 13 through 18 are schematic diagrams of the inductor elements (elements 120, 148, 150, 165, 166, and 169) that are placed in the lead wires to reduce harmful currents. As mentioned previously, significant stray capacitance can be produced along the lead wires, particularly for external pacers. As a result, Electromagnetic fields generated between the electrodes because of the radio-frequency field can produce dangerously high voltages across and currents flowing through the electrodes. To limit this current, and enhance patient safety, the inductor elements shown in FIGS. 13 through 18 are placed in the lead wires close to the electrodes. FIG. 13 shows the inductor elements 178 when a two-wire lead is used. FIG. 14 shows the inductor elements 180 when a two-wire shielded lead is used. FIG. 15 shows alternative inductor elements 182, which incorporate a capacitor 184, thus comprising an additional low-pass L-C filter. FIG. 16 shows the same alternative inductor elements 183 and a capacitor 185, as shown in FIG. 15, but using a shielded two-wire lead. FIG. 17 shows the inductor elements 186 used in a multi-lead shielded harness. FIG. 18 shows alternative inductor elements 188 used in a multi-lead shielded harness, which also includes capacitor components 190 connected to the shielding enclosure of the capacitors.

The leads can be used to measure ECG, EEG, or other electrical signals of physiological significance. FIGS. 13 through 18 show twisted leads, but it is to be understood that coaxial as well as other forms of lead wires could be used.

FIGS. 19 through 31 show various embodiments of the input radio-frequency filter, output radio-frequency filter, and combined input/output radio-frequency filter. According to the concepts of the present invention, there are many possible specific implementations of the radio-frequency filter design that will depend on: 1) whether two leads or multiple leads are used; 2) whether the leads are shielded; 3) whether single or multiple stage filtering is used; and 4) whether each radio-frequency filter is housed in a separate shielded enclosure.

It should be apparent that the filters could be placed either at the proximal end or the distal end of the pulse generator—lead assembly.

It will also become apparent that the same filter design principles can be used whether the filter is acting as an input filter for an ECG monitor, as separate input filters and output filters for a pacemaker, or as a single combined input/output filter for a pacemaker.

Figure 19:
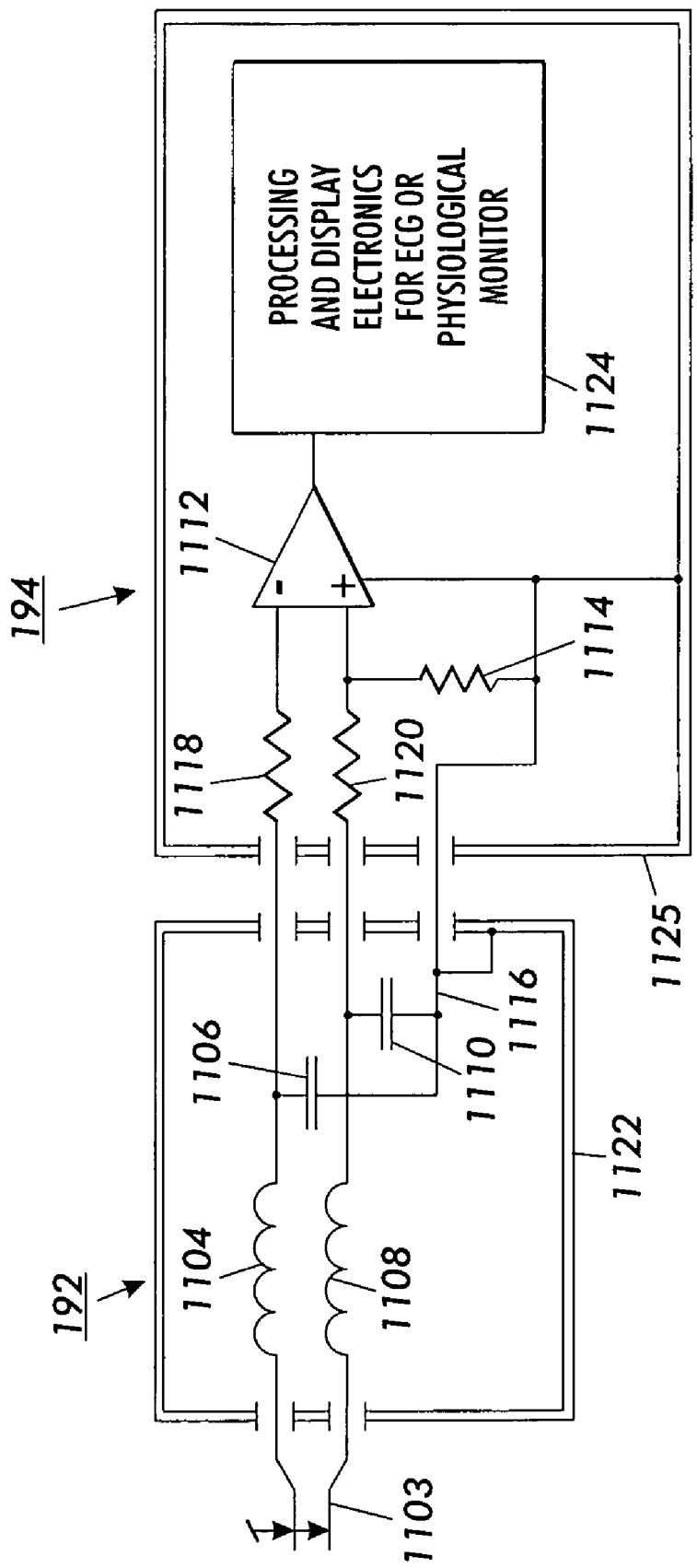
FIGS. 19 and 20 are block diagrams of ECG amplifiers with a one-stage radio-frequency filter design, according to the concepts of the present invention, for use with dual unshielded leads.
Figure 20:
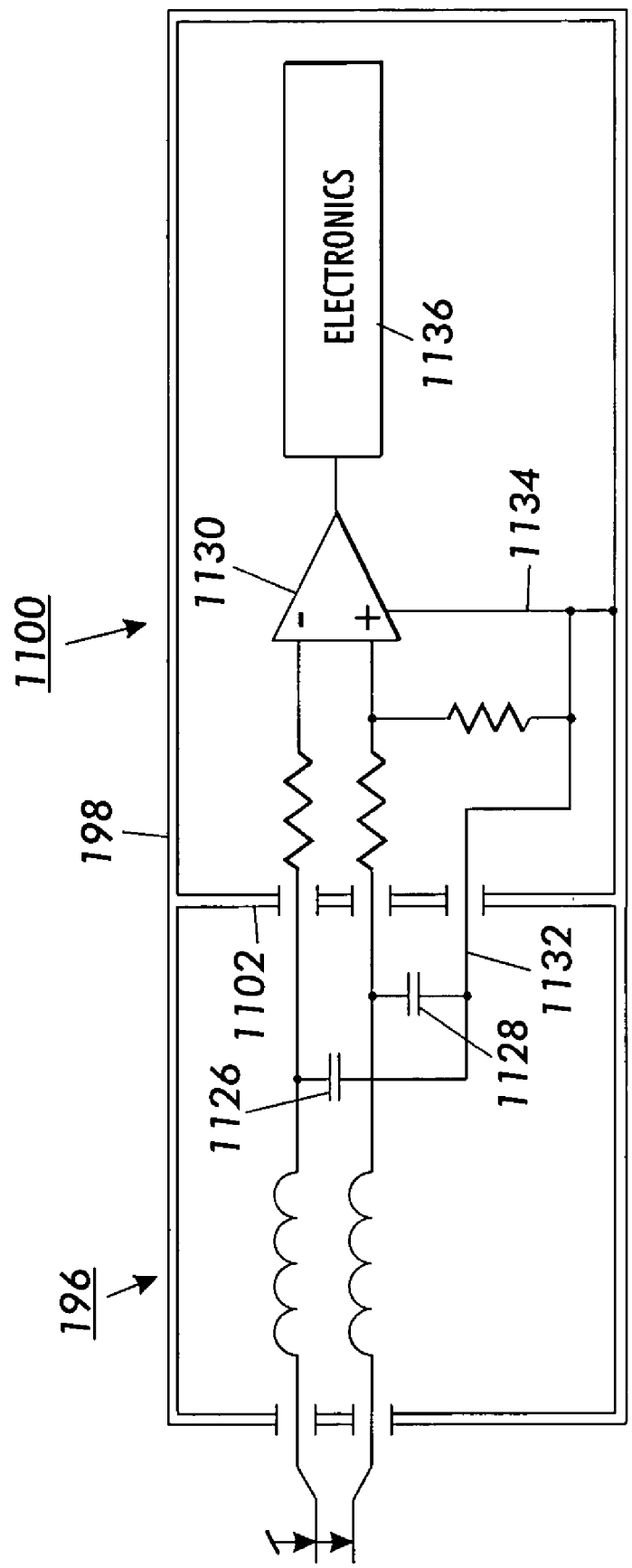
Figure 21:
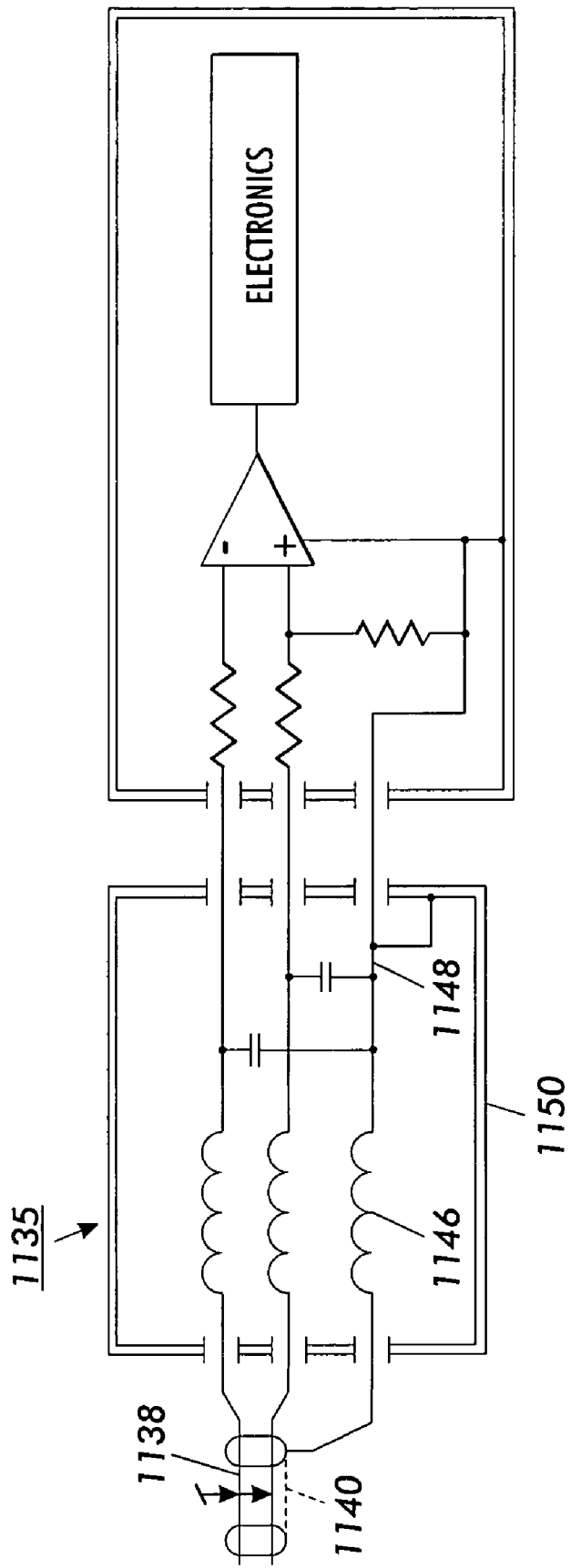
FIGS. 21 and 22 are block diagrams of ECG amplifiers with a one-stage radio-frequency filter design, according to the concepts of the present invention, for use with dual shielded leads.
Figure 22:
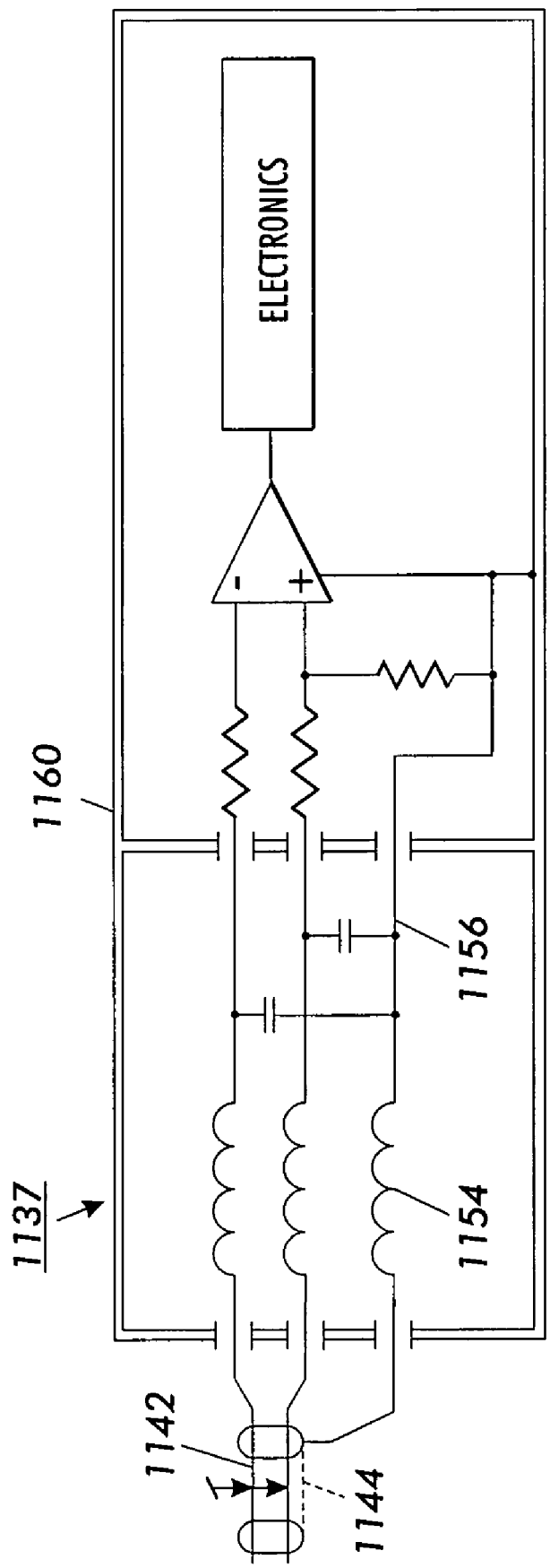

FIGS. 19 and 20 show one-stage filters for use with two unshielded leads. FIGS. 21 and 22 show alternative ways to shield the electronics.

FIG. 19 shows the input filter 192 in a separate shielded enclosure; whereas FIG. 20 shows the input filter 196 located in the same-shielded enclosure 198 as the processing electronics 1100 with an internal wall 1102 shielding the monitoring electronics 1100 from the input filter 196. (Whether one or two enclosures are used, the filter section should be shielded from the other circuitry.)

As can be seen in FIG. 19, each lead is connected to a separate low-pass filter. (Leads 1103 may be twisted to reduce electromagnetic interference). A first low-pass filter is made from inductor 1104 and capacitor 1106; and a second low-pass filter is made from inductor 1108 and capacitor 1110. Each low-pass filter offers approximately 100 dB signal attenuation in the radio-frequency frequency range of the magnetic-resonance imaging system and passes with little attenuation the desired physiological signal.

As mentioned previously, the L-C components must be high frequency elements retaining their desired characteristics throughout the frequency range. The output from the input filter 192 is connected to differential amplifier 1112. In order to properly utilize the differential amplifier 1112, the non-inverting input of the ECG amplifier 1112 is connected to the amplifier zero-signal reference terminal via a resistor 1114, as is well known in the art.

Obviously, any other method of converting a two to three conductor input may also be used. The two capacitors 1106, 1110 in the low-pass filters are referenced to a third wire 1116 that is connected to the shield surrounding the filter 1122 and also connected to the zero-signal reference terminal of the ECG amplifier 1112.

The ECG amplifier may be a single differential amplifier or a combination of multiple differential amplifiers. Alternatively, capacitors 1106, 1110 can be connected directly to the shield 1122 with a separate wire connecting the shield 1122 to the zero-signal reference terminal of the ECG amplifier 1112.

To improve the characteristics of the filter, resistors 1118, 1120 may be added between the input filter 192 and the input of the differential amplifier 1112. Just as the input filter 192 is enclosed in a shield 1122, the ECG amplifier 1112 and processor 1124 may also be enclosed in a separate shield 1125.

The shields may consist of patterned layers including conductive materials and non-conductive materials. The conductive materials of the present invention may be a metal, a carbon composite, nanotubes (wherein the nanotubes may be constructed from a carbon base or the nanotubes could be formed from other amalgams coated with the appropriate material(s)), metal-coated carbon filaments (wherein the metal may be one of the following metals: nickel, copper, cobalt, silver, gold, tin, or zinc), metal-coated ceramic filaments (wherein the metal may be one of the following metals: nickel, copper, cobalt, silver, gold, tin, or zinc), a composite of metal-coated carbon filaments and a polymer (wherein the polymer may be one of the following: polyether sulfone, silicone, polymide, polyvinylidene fluoride, or epoxy), a composite of metal-coated ceramic filaments and a polymer (wherein the polymer may be one of the following: polyether sulfone, silicone, polymide, polyvinylidene fluoride, or epoxy), a composite of metal-coated carbon filaments and a ceramic (wherein the ceramic may be one of the following: cement, silicates, phosphates, silicon carbide, silicon nitride, aluminum nitride, or titanium diboride), a composite of metal-coated ceramic filaments and a ceramic (wherein the ceramic may be one of the following: cement, silicates, phosphates, silicon carbide, silicon nitride, aluminum nitride, or titanium diboride), or a composite of metal-coated (carbon or ceramic) filaments (wherein the metal may be one of the following metals: nickel, copper, cobalt, silver, gold, tin, or zinc) and a polymer/ceramic combination (wherein the polymer may be one of the following: polyether sulfone, silicone, polymide, polyvinylidene fluoride, or epoxy and the ceramic may be one of the following: cement, silicates, phosphates, silicon carbide, silicon nitride, aluminum nitride, or titanium diboride).

FIG. 20 shows an alternative embodiment where the input filter 196 and processing electronics 1100 are housed in a single contiguous shielding enclosure 198. A separate metallic wall 1102 is used to shield the electronics 1100 from the input filter 196. In this embodiment, the two capacitors 1126, 1128 that make up the low-pass filters are connected to the zero-signal reference terminal of the differential amplifiers 1130 via a third reference wire 1132; the reference wire. 1132 and zero-signal reference terminal 1134 both connected to the pacemaker shielding case at a single point.

Both FIGS. 19 and 20 show processing electronics 1224, 1136 that are used to further process the signal obtained from the differential amplifiers 1112, 1130. The processing electronics may be used to process and display the ECG signal, in the case of an external monitor, or be used to process and control pacing in the case of a pacemaker. It is to be understood that the filter embodiments shown in FIGS. 19 and 20 could be used in a device that monitors physiologically significant electrical signals other than ECG.

FIGS. 21 and 22 show one-stage filter designs 1135 and 1137 that is preferred when the input leads are shielded. The design is identical to that shown in FIGS. 19 and 20, except that the lead shield must be coupled to the shield enclosure via a radio-frequency filter. To accomplish this, the lead shield 1140 of the leads 1138, in FIG. 21, is connected by an inductor 1146 to the third reference wire 1148, and the reference wire is connected to the filter's shielding enclosure 1150. Analogously, the shield 1144 of the leads 1142 in FIG. 22 is connected by an inductor 1154 to the reference wire 1156, connected in turn to the enclosure 1160. In order to further reduce the effects of the magnetic-resonance imaging system radio-frequency signal, more than one stage of filtering can be used.

Figure 23:
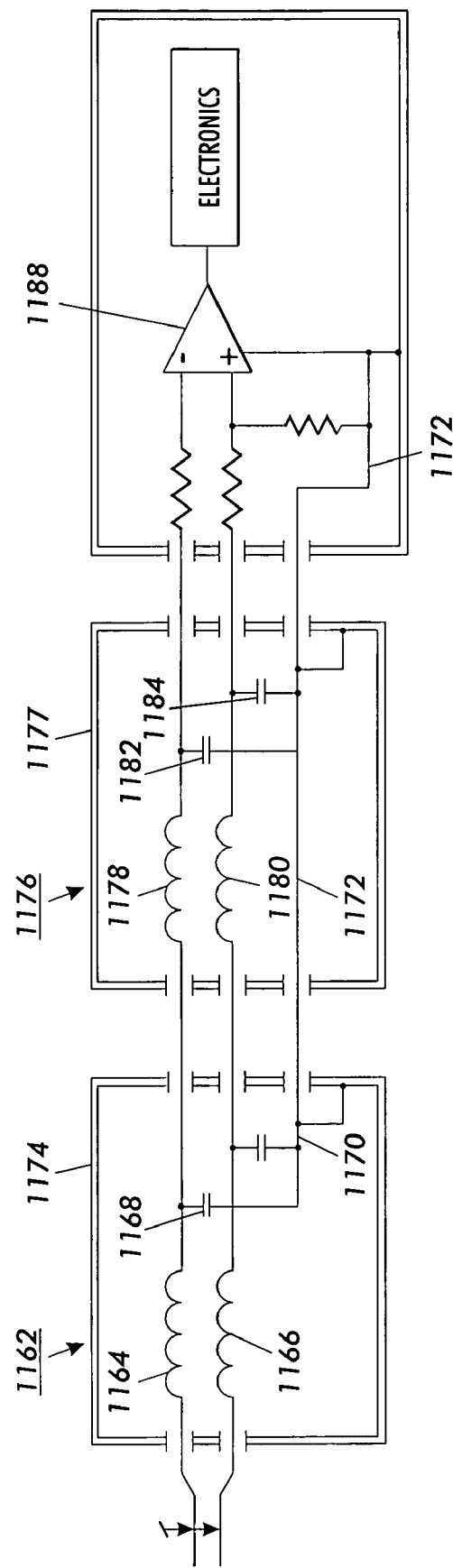
FIGS. 23 and 24 are block diagrams of ECG amplifiers with a multistage radio-frequency filter design, according to the concepts of the present invention, for use with dual unshielded leads.

In the embodiment shown in FIG. 23, two stages of filtering are used. Each filter stage is similar to the filter described in FIG. 19. Each input lead is connected to a low-pass filter. Each low-pass L-C filter has a capacitor connected to a reference wire that is connected to the shielding enclosure.

The first stage filter 1162 contains low-pass filters comprising inductors 1164, 1166 and capacitors 1168, 1170. Capacitors 1168, 1170 are coupled to a reference wire 1172 that is connected to the enclosure 1174. Similarly, the second filter stage 1176 contains low-pass filters made from inductors 1178, 1180 and capacitors 1182, 1184, with capacitors 1182, 1184 coupled to the reference wire 1172 that is connected to the shielding enclosure 1177. All the capacitors (1168, 1170, 1182 and 1184) used in the low-pass filters are connected to the reference wire 1172 which is connected to the zero-signal reference terminal of the differential amplifier 1188.

Each stage in FIG. 23 is housed in a separate shielding enclosure and each shielding enclosure is coupled to the reference wire 1172. It is understood that this concept can be extended to multistage filtering. The second stage 1176 could actually represent the Nth stage of a multistage filter, with each identical stage coupled together as shown.

Figure 24:
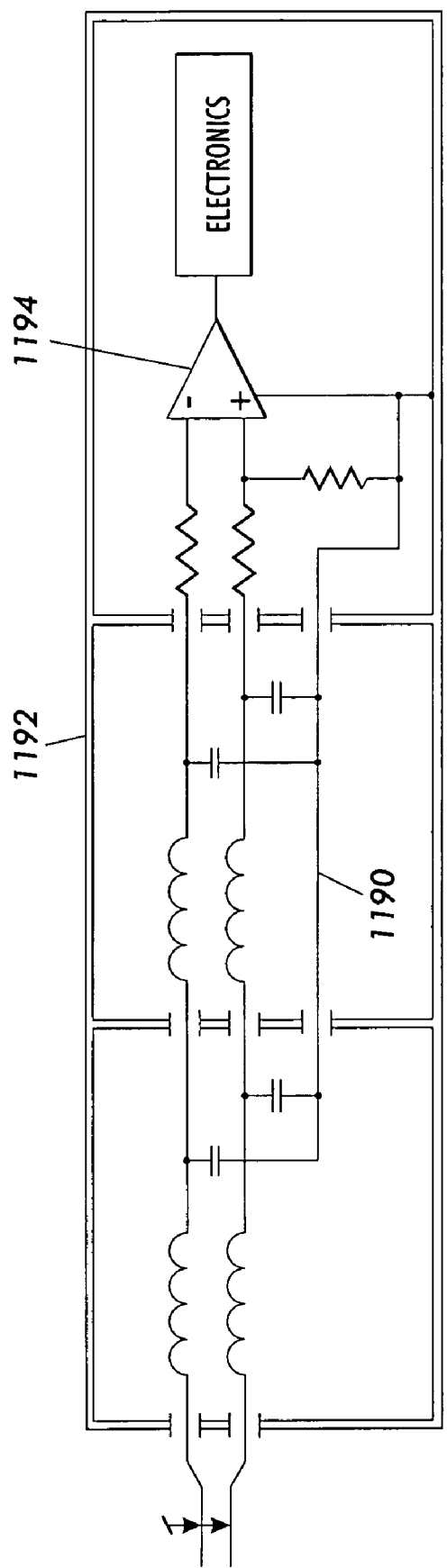

An alternative embodiment for multiple stage filtering is shown in FIG. 24. In this embodiment each filtering stage as well as the differential amplifier and the associated electronics are housed in the same contiguous shielding enclosure 1192. The filter design in this embodiment is identical to that shown in FIG. 20; however, the reference wire is only connected to the shielding case 1192 at a single point. In effect, the low-pass filters in each stage and the zero-signal reference terminal of the differential amplifier 1194 are all referred to the same point on the shielding enclosure. It is to be understood that the embodiment shown in FIG. 24 may also have three or more stages, each stage shielded and coupled together as shown.

Figure 25:
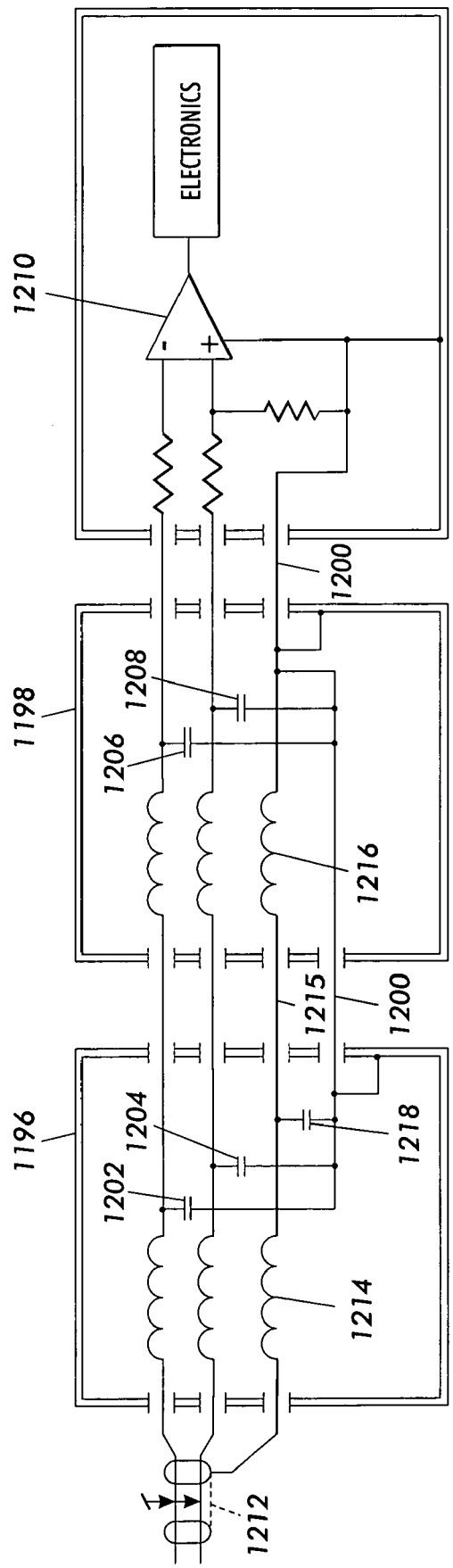
FIGS. 25 and 26 are block diagrams of ECG amplifiers with a multistage radio-frequency filter design, according to the concepts of the present invention, for use with dual shielded leads.

FIGS. 25 and 25 are schematic drawings of a two-stage filter for use with shielded leads. These filters are similar to the multistage filter embodiments shown in FIGS. 23 and 24, except that the lead shields are coupled via inductors to the reference wire in the last filter stage. FIG. 25 is a two-stage filter where each stage is separately isolated in enclosures 1196, 1198. Again, as in the previous embodiments, low-pass filters are connected in each input lead and referenced to a common reference line 1200 (i.e., capacitors 1202, 1204, 1206, and 1208 are connected to the reference line 1200).

The common reference line 1200 is connected to the shielding enclosure for each stage and is input to the zero-signal reference terminal of the differential amplifier 1210.

The lead shield 1212 is connected to inductor 1214 in the first filter stage and via line 1215 to inductor 1216 in the second filter stage. The inductor 1216 in the second, or final filter stage, is connected to the common reference line 1290. As discussed previously, the inductors 1214, 1216 provide high impedance to the undesirable high frequency radio-frequency voltages produced by the magnetic-resonance imaging system and prevent introduction of radio-frequency interference into the processing electronics via the common wire.

To increase performance, an additional capacitor 1218 may be connected between lines 1215 and 1200 in the first stage and any subsequent filter stage other than the last stage. Inductor 1214, coupled with capacitor 1218, provides a third low-pass filter.

Figure 26:
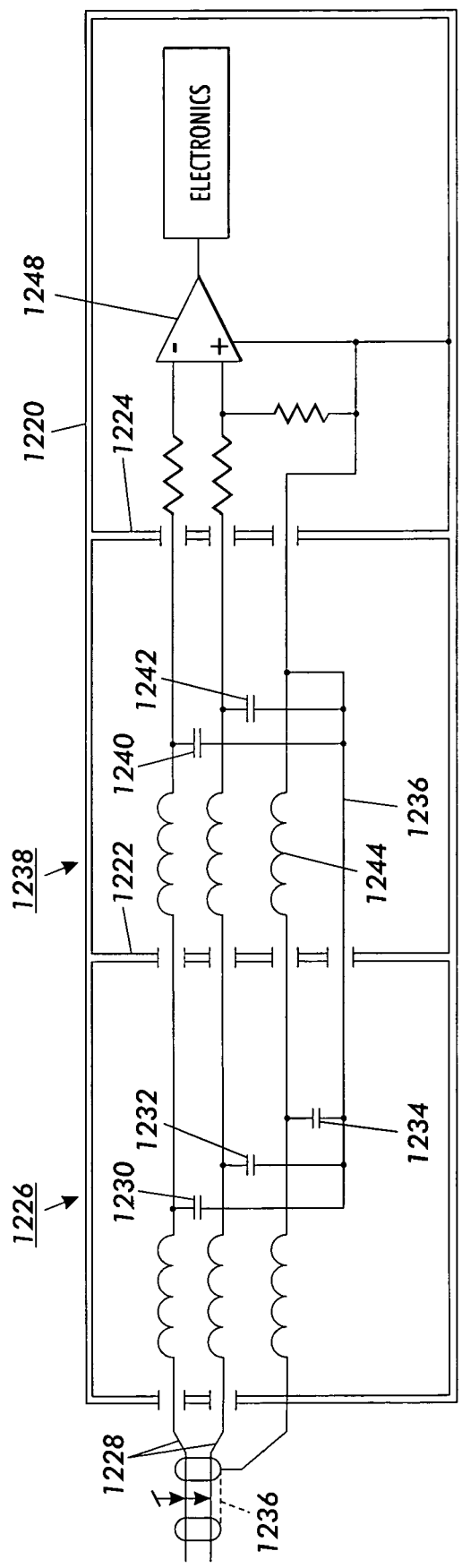

FIG. 26 is a multistage filter housed in a single shielding enclosure 1220 with separate walls 1222, 1224 isolating the filtering stages from each other and from the processing electronics. In the first stage 1226, each lead 1228 and the lead shield 1230 are coupled to low-pass filters referenced by capacitors 1230, 1232, and 1234 to a common reference line 1236. In the last stage 1238, only the two lead wires contain low-pass filters referenced by capacitors 1240, 1242 to the common reference line 1236. The lead shield 1230 is coupled via inductor 1244 directly to the reference line 1236.

As in the other embodiments, the reference line 1236 is connected to the zero-signal reference terminal of the differential amplifier 1248. Also as in the other embodiments, when a single case is used, the common reference line 1236 is connected to the shielding enclosure at a single point. It is of course understood that the two-stage filters shown in FIGS. 25 and 26 could be easily extended to multiple stage filtering with each stage connected as described.

Figure 27:
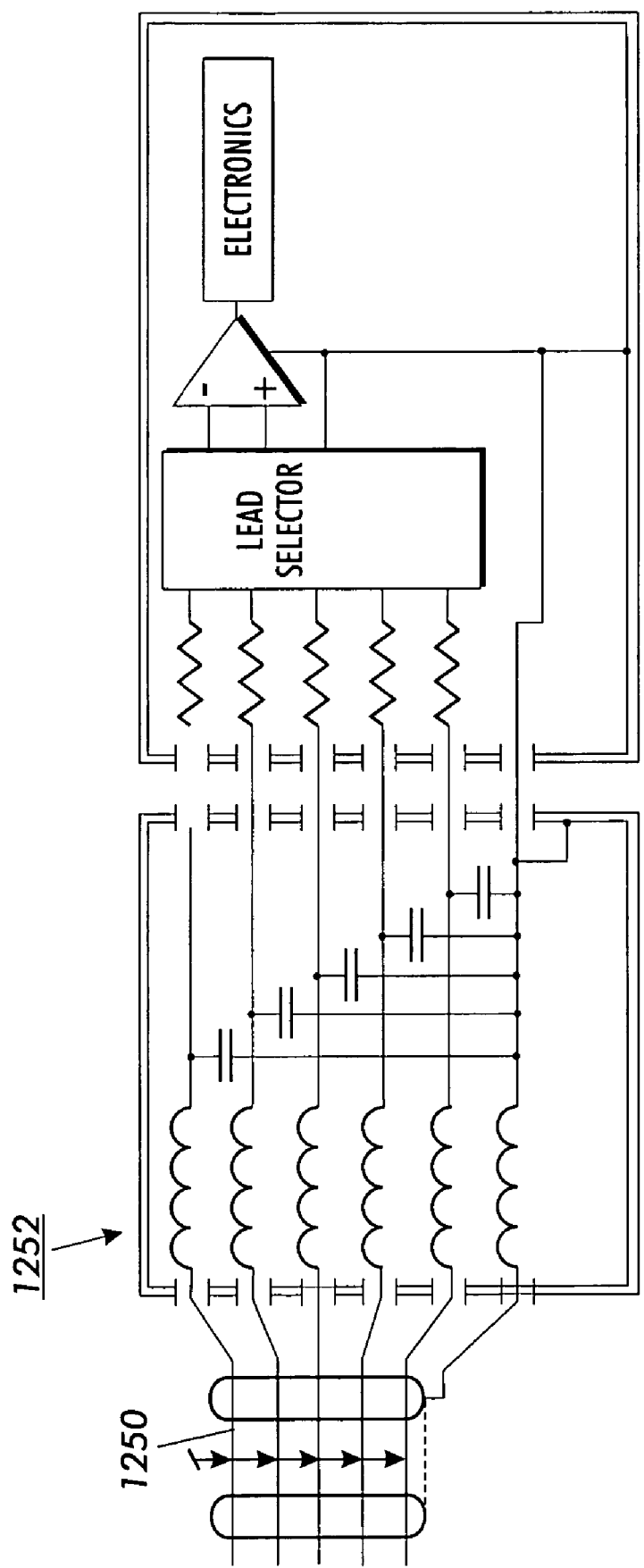
FIGS. 27 and 28 are block diagrams of ECG amplifiers with a multistage radio-frequency filter design, according to the concepts of the present invention, for use with a multi-lead ECG harness.
Figure 28:
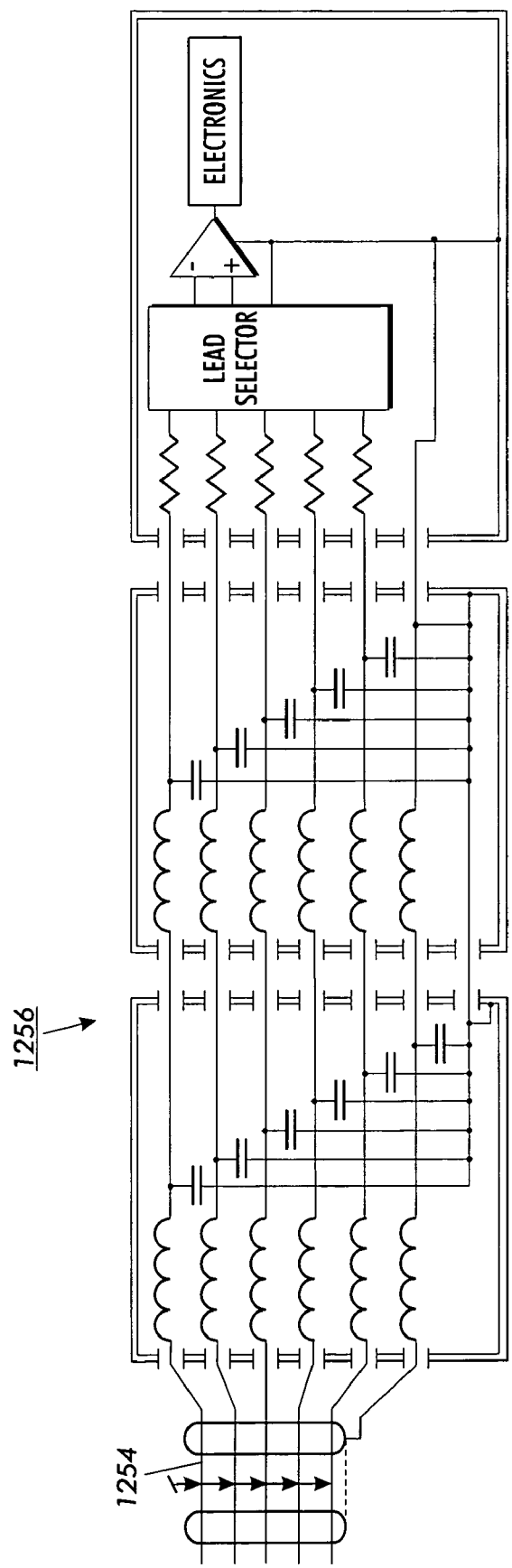

FIGS. 27 and 28 show an extension of the single and multiple stage filtering to multiple lead shielded ECG harness. In FIG. 27, a five conductor shielded cable 1250 is filtered by a single stage filter 1252. In FIG. 28, a five conductor shielded cable 1254 is filtered by a multiple stage filter 1256.

Figure 29:
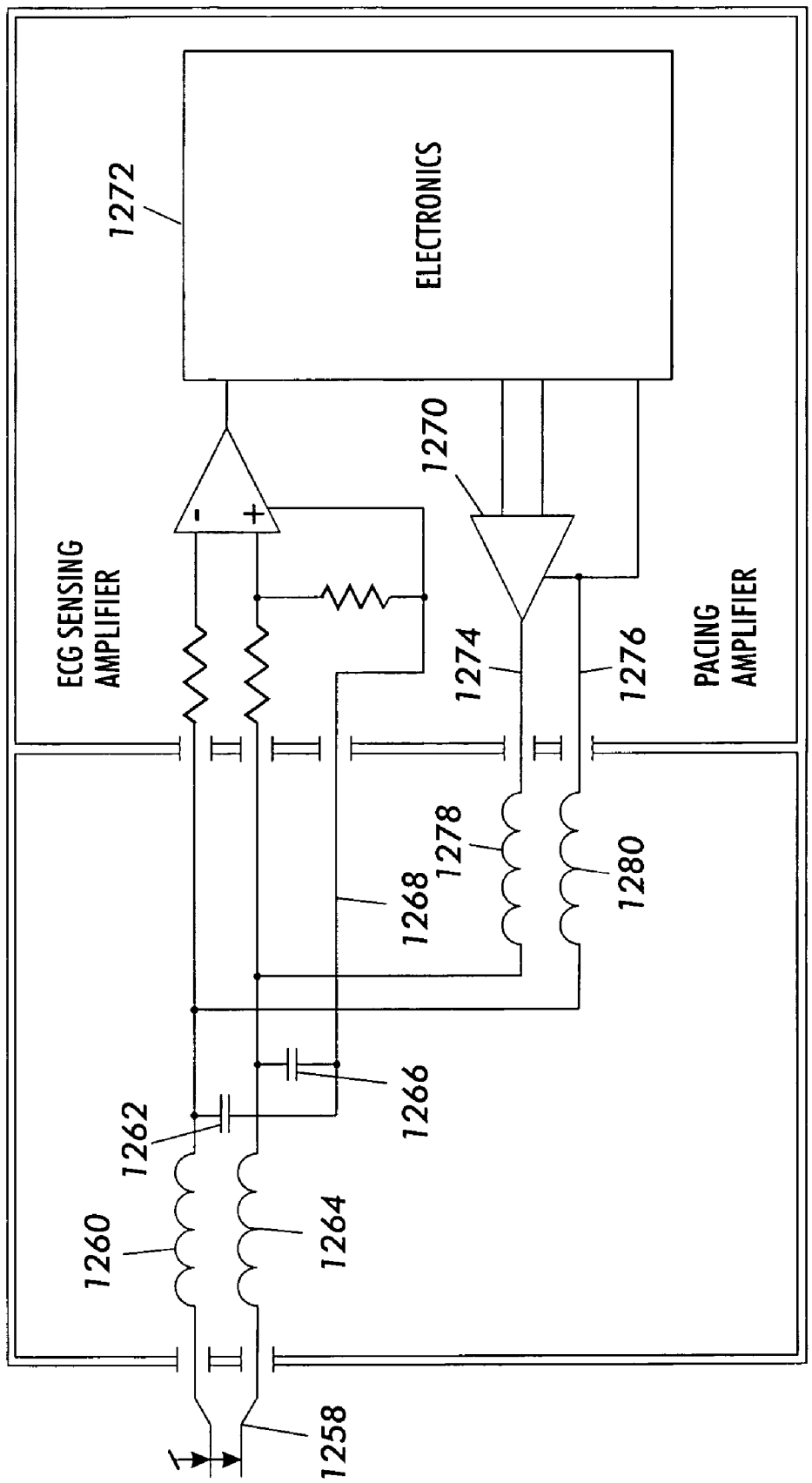
FIG. 29 is a block diagram of a magnetic-resonance imaging safe implantable pacemaker in accordance with the present invention.

Thus far, the filters have been described as input filters. However, as shown in FIG. 29, the filters can operate as both input and output filters. As generally true in pacemakers, the lead pair 1258 can be used to sense electrical activity of the heart as well as to pace the heart. As shown previously, low pass filters (i.e., inductor 1260/capacitor 1262 pair and inductor 1264/capacitor 1266 pair) for each lead are referenced to a common reference line 1268. The reference line 1268 then connects to the zero-signal reference terminal of the differential amplifier and to the shielding enclosure. A pacing amplifier 1270 in controlled by electronics 1272 to generate a pacing signal. The pacing signal is connected via lines 1274, 1276 through the filter, to the leads 1258. Two inductors 1278, 1280 are placed in lines 1274, 1276 to further prevent any current generated by the magnetic-resonance imaging system from affecting the pacing amplifier 1270; the inductors 1278, 1 provide an additional high impedance to the high frequency radio-frequency signals produced by the magnetic-resonance imaging system.

Connecting the pacing amplifier to the leads 1258 via the filter can be used with each of the filter embodiments described above. In multistage filtering embodiments, pacing amplifiers would be preferably connected into the last filtering stage.

Figure 30:
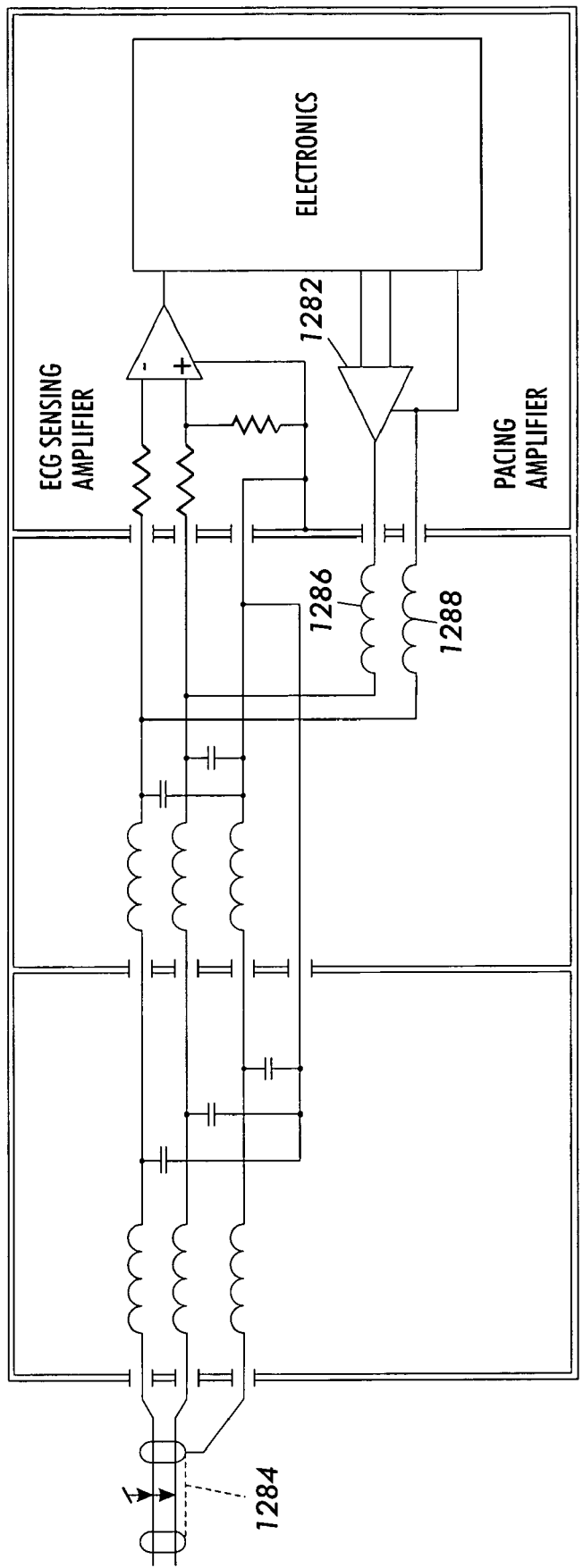
FIG. 30 is a block diagram of a magnetic-resonance imaging safe implantable pacemaker using a multistage radio-frequency filter, according to the concepts of the present invention.

FIG. 30 is an exemplary embodiment, showing how the pacing amplifier 1282 can be connected via a multi-stage filter to the shielded pacing/sensing leads 1234. The pacing amplifier 1282 is connected via inductors 1286 and 1288 to the lead wires in the last stage of the filter. As discussed above, the inductors 1286, 1288 provide additional protection from the high frequency radio-frequency signals generated by the magnetic-resonance imaging system.

Figure 31:
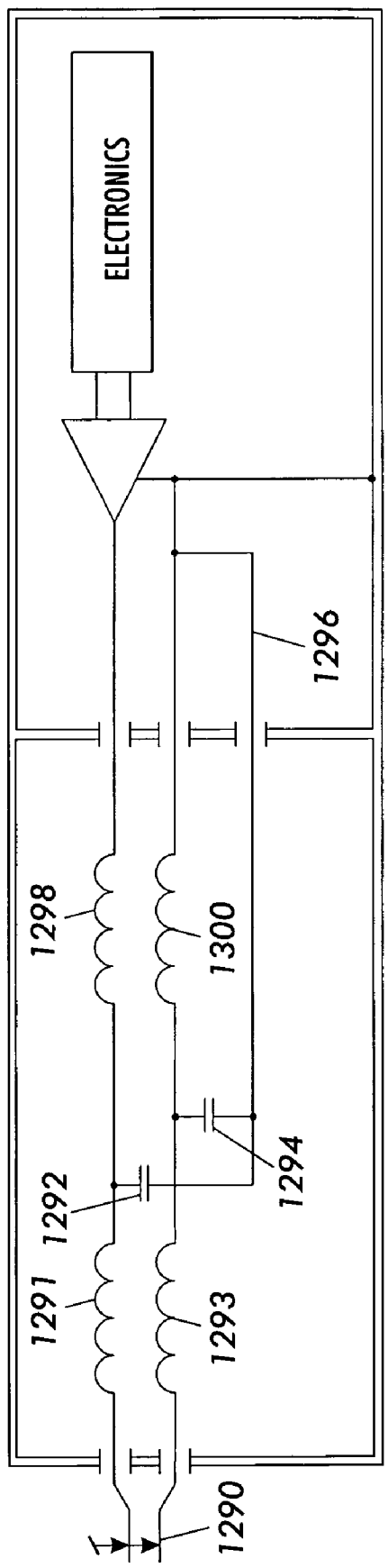
FIG. 31 is a block diagram of an implantable stimulator capable of operating in a magnetic-resonance imaging system, in accordance with the present invention.

There are an unlimited number of ways in which the filters described herein can be connected to both sensing electronic and pacing amplifiers. In fact, the same filter design can be used in stimulators, as shown in FIG. 31, where only a pacing signal is produced.

The filter design is identical to those described previously. The leads 1290 are each connected to low pass filters (inductor 1291/capacitor 1292 pair and inductor 1293/capacitor 1294 pair) that are referred by capacitors 1292, 1294 to a common reference line 1296. Inductors 1298, 1300 provide additional isolation to protect the pacing amplifier. The filter design for stimulation use only can be extended to multistage embodiments as described above.

In order to protect the implantable pacemaker elements from the effects of the radio-frequency signals produced by the magnetic-resonance imaging system, it is necessary to surround the components with a radio-frequency shield.

This shielding may consist of patterned layers including conductive materials and non-conductive materials. The conductive materials of the present invention may be a metal, a carbon composite, nanotubes (wherein the nanotubes may be constructed from a carbon base or the nanotubes could be formed from other amalgams coated with the appropriate material(s)), metal-coated carbon filaments (wherein the metal may be one of the following metals: nickel, copper, cobalt, silver, gold, tin, or zinc), metal-coated ceramic filaments (wherein the metal may be one of the following metals: nickel, copper, cobalt, silver, gold, tin, or zinc), a composite of metal-coated carbon filaments and a polymer (wherein the polymer may be one of the following: polyether sulfone, silicone, polymide, polyvinylidene fluoride, or epoxy), a composite of metal-coated ceramic filaments and a polymer (wherein the polymer may be one of the following: polyether sulfone, silicone, polymide, polyvinylidene fluoride, or epoxy), a composite of metal-coated carbon filaments and a ceramic (wherein the ceramic may be one of the following: cement, silicates, phosphates, silicon carbide, silicon nitride, aluminum nitride, or titanium diboride), a composite of metal-coated ceramic filaments and a ceramic (wherein the ceramic may be one of the following: cement, silicates, phosphates, silicon carbide, silicon nitride, aluminum nitride, or titanium diboride), or a composite of metal-coated (carbon or ceramic) filaments (wherein the metal may be one of the following metals: nickel, copper, cobalt, silver, gold, tin, or zinc) and a polymer/ceramic combination (wherein the polymer may be one of the following: polyether sulfone, silicone, polymide, polyvinylidene fluoride, or epoxy and the ceramic may be one of the following: cement, silicates, phosphates, silicon carbide, silicon nitride, aluminum nitride, or titanium diboride).

In the various embodiments described above with respect to FIG. 10 through 31, a common reference line was described in the context of a unipolar lead system. It is noted that the common reference line may not be a separate line, but the common reference line may be one of the leads in a bipolar lead system. Moreover, the common reference line may a type of ground path (or line) or signal return path (or line). The common reference line merely provides electrical ground for the filters.

In summary the present invention, as described above, is an electromagnetic shield having a first patterned layer having non-conductive materials and conductive materials and a second patterned layer having non-conductive materials and conductive materials. The conductive materials in the first patterned layer may be randomly located or located in a predetermined segmented pattern. Moreover, the conductive materials in the first patterned layer may be located in a predetermined segmented pattern with respect to locations of the conductive materials in the second patterned layer. The electromagnetic shield may further include a non-conductive layer between the first and second patterned layers such that the conductive materials in the first patterned layer can overlap the conductive materials in the second patterned layer with respect to a direction substantially perpendicular to a planar surface of the second patterned layer.

Therefore, the present invention provides a patterned shielding that substantially prevents undesired radiation from entering the lead from the radial direction or electrical component and also substantially prevents the formation or inducement of eddy currents on the surface of the shielding, which are induced by the pulsing of the radiation or changing magnetic field of the radiation. More specifically, the conductive material in a shielding layers of the present invention is patterned or segmented so that the conductive material is literally broken up to limit the build up of eddy currents induced by the changing magnetic fields.

Moreover, the present invention can reduce specific absorption ratio by altering the magnetic-resonance imaging acquisition process by altering the imaging pulse sequence and/or changing the timing parameters. Furthermore, the radio-frequency excitation cycle may be interrupted to allow for cooling. Therefore if a threshold temperature level is exceeded, the imaging acquisition can be halted until the tissue temperature is at an acceptable level.

While various examples and embodiments of the present invention have been shown and described, it will be appreciated by those skilled in the art that the spirit and scope of the present invention are not limited to the specific description and drawings herein, but extend to various modifications and changes all as set forth in the following claims.

What is claimed is:

1. A medical assist system, comprising:
   a primary device housing; said primary device housing having a control circuit therein;
   a lead system to provide an electrical path between a tissue region and said primary device housing; and
   a shielding formed around said lead system to shield said lead system from electromagnetic interference;
   said shielding being formed of a first layer patterned with non-conductive materials and conductive materials and a second layer patterned with non-conductive materials and conductive materials;
   wherein the conductive materials of the first layer are patterned in a direction substantially parallel to an axis of the lead system such that each of the conductive materials is physically separated from the other conductive materials of the first layer;
   wherein the conductive materials of the second layer are patterned in a direction substantially parallel to an axis of the lead system such that each of the conductive materials is physically separated from the other conductive materials of the second layer; and
   wherein the conductive materials of the first layer and the conductive materials of the second layer are patterned in a direction substantially perpendicular to the axis of the lead system such that each of the conductive materials of the first layer is electrically isolated from the conductive materials in the second layer.

2. The medical assist system as claimed in claim 1, wherein said conductive material is a metal to shield said lead system from electromagnetic interference.

3. The medical assist system as claimed in claim 1, wherein said conductive material includes metal-coated carbon filaments to shield said lead system from electromagnetic interference.

4. The medical assist system as claimed in claim 1, wherein said conductive material is a polymer composite to shield said lead system from electromagnetic interference.

5. The medical assist system as claimed in claim 1, further comprising a non-permeable diffusion resistant biocompatible material covering said shielding.

6. The medical assist system as claimed in claim 1, wherein said shielding is formed around said primary housing to shield said primary housing from electromagnetic interference.

7. The medical assist system as claimed in claim 1, wherein said first and second layers are constructed of first and second patterned sheaths, each patterned sheath having non-conductive materials and conductive materials.

8. The medical assist system as claimed in claim 7, wherein said non-conductive materials in one of said first and second patterned sheaths are randomly located.

9. The medical assist system as claimed in claim 7, wherein said non-conductive materials in said first and second patterned sheaths are located in a predetermined segmented pattern.

10. The medical assist system as claimed in claim 7, wherein said non-conductive materials in said first and second patterned sheaths are located in a predetermined segmented pattern with respect to a direction substantially parallel with an axis of said lead system.

11. The medical assist system as claimed in claim 10, wherein said non-conductive materials in said first and second patterned sheaths are located in a predetermined segmented pattern with respect to a direction substantially perpendicular with an axis of said lead system.

12. The medical assist system as claimed in claim 7, wherein said non-conductive materials in said first and second patterned sheaths are located in a predetermined segmented pattern with respect to a direction substantially perpendicular with an axis of said lead system.

13. The medical assist system as claimed in claim 1, wherein said lead system includes an electrical lead.

14. The medical assist system as claimed in claim 13, wherein said electrical lead is one of a bipolar lead and a unipolar lead.

15. The medical assist system as claimed in claim 13, wherein said lead system includes a combination of unipolar and bipolar leads.

16. The medical assist system as claimed in claim in 13, wherein said lead system includes an insulator layer between said electrical lead and said shielding.

17. The medical assist system as claimed in claim 1, wherein said lead system includes an intraluminal coil.

18. The medical assist system as claimed in claim 1, wherein said lead system includes a catheter guide wire.

19. The medical assist system as claimed in claim 1, wherein said lead system includes a lead for a neurostimulation probe.

20. The medical assist system of claim 1, wherein the first layer is immediately adjacent to the second layer.

21. A medical assist device, comprising:
a primary device housing; and said primary device housing having a control circuit therein; and
a shielding formed around said primary device housing to shield said primary device housing and any circuits therein from electromagnetic interference; said shielding being formed of a first layer patterned with non-conductive materials and conductive and a second layer patterned with non-conductive materials and conductive material;
wherein the conductive materials of the first layer are patterned in a direction substantially parallel to an axis of the lead system such that each of the conductive materials is physically separated from the other conductive materials of the first layer;
wherein the conductive materials of the second layer are patterned in a direction substantially parallel to an axis of the lead system such that each of the conductive materials is physically separated from the other conductive materials of the second layer; and
wherein the conductive materials of the first layer and the conductive materials of the second layer are patterned in a direction substantially perpendicular to the axis of the lead system such that each of the conductive materials of the first layer is electrically isolated from the conductive materials in the second layer.

22. The medical assist device as claimed in claim 21, wherein said conductive material is a metal to shield said primary housing from electromagnetic interference.

23. The medical assist device as claimed in claim 21, wherein said conductive material includes metal-coated carbon filaments to shield said primary housing from electromagnetic interference.

24. The medical assist device as claimed in claim 21, wherein said conductive material is a polymer composite to shield said primary housing from electromagnetic interference.

25. The medical assist device as claimed in claim 21, further comprising a non-permeable diffusion resistant biocompatible material covering said shielding.

26. The medical assist system as claimed in claim 21, wherein said conductive material comprises nanotubes to shield said lead system from electromagnetic interference.

27. The medical assist device as claimed in claim 21, wherein said conductive material comprises nanotubes to shield said primary housing from electromagnetic interference.

28. The medical assist system of claim 21, wherein the first layer is immediately adjacent to the second layer.

29. A medical assist system, comprising:
a primary device housing; said primary device housing having a control circuit therein;
a lead system to provide an electrical path between a tissue region and said primary device housing; and
a shielding formed around said lead system to shield said lead system from electromagnetic interference; said shielding being formed of a first layer of an apertured conductive material; said apertured conductive material having a maximum aperture dimension of 0.01 millimeters to 10 millimeters, and a second layer of an apertured conductive material said second layer of apertured conductive material having a maximum aperture dimension of 0.01 millimeters to 10 millimeters;
wherein the apertured conductive materials of the first layer are patterned in a direction substantially parallel to an axis of the lead system such that each of the apertured conductive materials is physically separated from the other conductive materials of the first layer;
wherein the apertured conductive materials of the second layer are patterned in a direction substantially parallel to an axis of the lead system such that each of the apertured conductive materials is physically separated from the other conductive materials of the second layer; and
wherein the apertured conductive materials of the first layer and the apertured conductive materials of the second layer are patterned in a direction substantially perpendicular to the axis of the lead system such that each of the apertured conductive materials of the first layer is electrically isolated from the apertured conductive materials in the second layer.

30. The medical assist system as claimed in claim 29, wherein said conductive material is a metal to shield said lead system from electromagnetic interference.

31. The medical assist system as claimed in claim 29, wherein said conductive material includes metal-coated carbon filaments to shield said lead system from electromagnetic interference.

32. The medical assist system as claimed in claim 29, wherein said conductive material is a polymer composite to shield said lead system from electromagnetic interference.

33. The medical assist system as claimed in claim 29, further comprising a non-permeable diffusion resistant biocompatible material covering said shielding.

34. The medical assist system as claimed in claim 29, wherein said shielding formed around said primary housing to shield said primary housing from electromagnetic interference.

35. The medical assist system as claimed in claim 34, wherein said conductive material is a metal to shield said lead system and said primary housing from electromagnetic interference.

36. The medical assist system as claimed in claim 34, wherein said conductive material includes metal-coated carbon filaments to shield said lead system and said primary housing from electromagnetic interference.

37. The medical assist system as claimed in claim 34, wherein said conductive material is a polymer composite to shield said lead system and said primary housing from electromagnetic interference.

38. The medical assist system as claimed in claim 29, wherein apertures of said apertured conductive material of shielding are constructed from non-conductive materials being dispersed in said conductive material.

39. The medical assist system as claimed in claim 38, wherein said non-conductive materials are randomly located.

40. The medical assist system as claimed in claim 38, wherein said non-conductive materials are located in a predetermined segmented pattern.

41. The medical assist system as claimed in claim 29, wherein said first and second layers are constructed of first and second patterned sheaths, each patterned sheath having non-conductive materials and conductive material.

42. The medical assist system as claimed in claim 41, wherein apertures of said apertured conductive material of shielding are constructed from non-conductive materials being dispersed in said conductive material.

43. The medical assist device of claim 29, wherein the first layer is immediately adjacent to the second layer.

44. A medical assist device, comprising:
a primary device housing; and said primary device housing having a control circuit therein;

a shielding formed around said primary device housing to shield said primary device housing and any circuits therein from electromagnetic interference; said shielding being formed of a first layer of a an apertured conductive material; said apertured conductive material having a maximum aperture dimension of 0.01 millimeters to 10 millimeters, and a second layer of a apertured conductive material said second layer of apertured conductive material having a maximum aperture dimension of 0.01 millimeters to 10 millimeters;

wherein the apertured conductive materials of the first layer are patterned in a direction substantially parallel to an axis of the lead system such that each of the apertured conductive materials is physically separated from the other conductive materials of the first layer;

wherein the apertured conductive materials of the second layer are patterned in a direction substantially parallel to an axis of the lead system such that each of the apertured conductive materials is physically separated from the other conductive materials of the second layer; and wherein the apertured conductive materials of the first layer and the apertured conductive materials of the second layer are patterned in a direction substantially perpendicular to the axis of the lead system such that each of the apertured conductive materials of the first layer is electrically isolated from the apertured conductive materials in the second layer.

45. The medical assist device as claimed in claim 44, wherein said conductive material is a metal to shield said primary housing from electromagnetic interference.

46. The medical assist device as claimed in claim 44, wherein said conductive material includes metal-coated carbon filaments to shield said primary housing from electromagnetic interference.

47. The medical assist device as claimed in claim 44, wherein said conductive material is a polymer composite to shield said primary housing from electromagnetic interference.

48. The medical assist device as claimed in claim 44, further comprising a non-permeable diffusion resistant biocompatible material covering said shielding.

49. The medical assist system as claimed in claim 44, wherein said conductive material comprises nanotubes to shield said lead system from electromagnetic interference.

50. The medical assist device as claimed in claim 44, wherein said conductive material comprises nanotubes to shield said primary housing from electromagnetic interference.

51. The medical assist system as claimed in claim 44, wherein apertures of said apertured conductive material of shielding are constructed from non-conductive materials being dispersed in said conductive material.

52. The medical assist system as claimed in claim 51, wherein said non-conductive materials are randomly located.

53. The medical assist system as claimed in claim 51, wherein said non-conductive materials are located in a predetermined segmented pattern.

54. The medical assist device of claim 44, wherein the first layer is immediately adjacent to the second layer.

* * * * *